US009108005B2

(12) United States Patent
Agee et al.

(10) Patent No.: US 9,108,005 B2
(45) Date of Patent: Aug. 18, 2015

(54) TREATMENT OF CARPAL TUNNEL SYNDROME BY INJECTION OF THE FLEXOR RETINACULUM

(71) Applicant: JOHN M. AGEE, TRUSTEE OF THE JOHN M. AGEE TRUST OF AUG. 15, 1996, Sacramento, CA (US)

(72) Inventors: John M. Agee, Cameron Park, CA (US); Ben C. Goss, Athens, GA (US); Francis C. King, Sacramento, CA (US); Jeffrey Woodhouse, Sacramento, CA (US)

(73) Assignee: JOHN M. AGEE AND KAREN K. AGEE, TRUSTEES OF THE JOHN M. AGEE TRUST, Sacramento, CA (US)

( * ) Notice: Subject to any disclaimer, the term of this patent is extended or adjusted under 35 U.S.C. 154(b) by 0 days.

(21) Appl. No.: 14/153,785

(22) Filed: Jan. 13, 2014

(65) Prior Publication Data
US 2014/0193394 A1 Jul. 10, 2014

Related U.S. Application Data

(62) Division of application No. 12/732,047, filed on Mar. 25, 2010, now Pat. No. 8,702,654.

(60) Provisional application No. 61/163,165, filed on Mar. 25, 2009.

(51) Int. Cl.
*A61M 5/42* (2006.01)
*A61B 17/32* (2006.01)
(Continued)

(52) U.S. Cl.
CPC ............... *A61M 5/427* (2013.01); *A61B 17/32* (2013.01); *A61B 17/320036* (2013.01); *A61B 17/3403* (2013.01); *A61K 9/0019* (2013.01); *A61K 31/56* (2013.01); *A61K 38/4886* (2013.01);
(Continued)

(58) Field of Classification Search
CPC .......... A61B 17/32; A61B 17/320036; A61B 17/3403; A61B 2017/3405; A61B 2017/3407; A61B 2017/3409; A61B 2017/3413; A61M 5/427; A61M 5/52; A61M 2210/083
USPC .............. 604/93.01, 117, 500, 505–508, 510, 604/511, 513; 128/897, 898
See application file for complete search history.

(56) References Cited

U.S. PATENT DOCUMENTS 4,885,687 A * 12/1989 Carey ............................ 434/261
4,962,770 A 10/1990 Agee et al.
(Continued)

OTHER PUBLICATIONS

Sucher, B.—"Myofascial manipulative release of carpal tunnel syndrome: Documentation with magnetic resonance imaging"—Jour. Am. Osteopath Assoc., 1993, vol. 93, pp. 1273-1278.
(Continued)

*Primary Examiner* — Kami A Bosworth
(74) *Attorney, Agent, or Firm* — John P. O'Banion

(57) ABSTRACT

An apparatus and method for identifying the flexor retinaculum of the carpal tunnel, injecting an effective amount of an agent into at least a portion of flexor retinaculum or tissue adjacent thereto, wherein the agent is configured to weaken the flexor retinaculum. The system may further include means for increasing the tensile stress in the flexor retinaculum post-injection using hand exercises, thereby weakening its structural integrity and decreasing the pressure within the carpal tunnel that impairs median nerve function.

19 Claims, 20 Drawing Sheets

(51) Int. Cl.
| | |
|---|---|
| A61B 17/34 | (2006.01) |
| A61K 31/56 | (2006.01) |
| A61K 9/00 | (2006.01) |
| A61K 38/48 | (2006.01) |
| A61M 5/52 | (2006.01) |

(52) U.S. Cl.
CPC ......... *A61M 5/52* (2013.01); *A61B 2017/3413* (2013.01); *A61M 2210/083* (2013.01)

(56) References Cited

U.S. PATENT DOCUMENTS

| | | | | |
|---|---|---|---|---|
| 4,963,147 | A | | 10/1990 | Agee et al. |
| 5,089,000 | A | | 2/1992 | Agee et al. |
| 5,179,963 | A | * | 1/1993 | Berger .......................... 128/898 |
| 5,306,284 | A | | 4/1994 | Agee et al. |
| 5,533,526 | A | | 7/1996 | Goldberg |
| 5,589,171 | A | | 12/1996 | Wegman |
| 5,950,628 | A | | 9/1999 | Dunfee |
| 6,086,872 | A | | 7/2000 | Wegman |
| 6,146,347 | A | | 11/2000 | Porrata |
| 2004/0098005 | A1 | * | 5/2004 | Mirza et al. ................... 606/170 |
| 2008/0009736 | A1 | * | 1/2008 | Amadio et al. ............... 600/453 |
| 2009/0010918 | A1 | | 1/2009 | Badalemente et al. |

OTHER PUBLICATIONS

Allampallam, K. et al.—"Explant Culture, Immunofluorescence and Electron-Microscopic Study of Flexor Retinaculum in Carpal Tunnel Syndrome"—Journ. Occup. Environ. Med., 1996, vol. 38, pp. 264-271.
Stransky, G. et al.—"Collagen Dysplasia in Idiopathic Carpal Tunnel Syndrome"—Pathol. Res. Pract., 1989, vol. 185, pp. 795-798.
Sucher, B.—"Palpatory diagnosis and manipulative management of carpal tunnel sydrome"—Jour. Am. Osteopath. Assoc., 1994, vol. 94, pp. 647-663.
Nakamichi, K. et al.—"Transverse Sliding of the Median Nerve Beneath the Flexor Retinaculum"—Jour. of Hand Surgery (British Volume), 1992, 17B, pp. 213-216.
Richman, J. et al.—"Carpal tunnel syndrome: Morphologic changes after release of the transverse carpal ligament"—Jour. of Hand Surgery (American Volume), 1989, 14A, pp. 852-857.
Werner, C. et al.—"Pressure and Nerve Lesion in the Carpal Tunnel"—Acta Orthop., 1983, vol. 54, pp. 312-316.
Goodman, C. et al.—"Comparison of Carpal Tunnel Canal Pressure in Parapalegic and Nonparapalegic Subjects: Clinical Implications"—Plastic Reconstruc. Surgery, 2001, vol. 107, pp. 1464-1471.
Okutsu, I. et al.—"Complete Endoscopic Carpal Canal Decompression"—Amer. Journ. Orthop., 1996, vol. 25, pp. 365-368.
Keir, P. et al.—"Fingertip Loading and Carpal Tunnel Pressure: Differences Between a Pinching and a Pressing Task"—Journ. of Orthopaedic Research, 1998, vol. 16, pp. 112-115.
Rempel, D. et al.—"Effects of Static Fingertip Loading on Carpal Tunnel Pressure"—Journ. of Orthopaedic Research, 1997, vol. 15, pp. 422-426.
Luchetti, R. et al.—"Correlation of Segmental Carpal Tunnel Pressures with Changes in Hand and Wrist Positions in Patients with Carpal Tunnel Syndrome and Controls"—Journ. of Hand Surgery, (British Volume), 1998, vol. 23B, pp. 598-602.
Bauman, T. et al.—"The Acute Carpal Tunnel Syndrome"—Clinical Orthop. Relat. Res, 1981, vol. 156, pp. 151-156.
Fuller, D. et al.—"Carpal Canal Pressures After Volar Plating of Distal Radius Fractures"—Journ. of Hand Surgery (British Volume), 2006, vol. 31B, pp. 236-239.
Luchetti, R. et al.—"Carpal-tunnel pressure"—Acta Orthop, 1989, vol. 60, 397-399.
Lucehtti, R. et al.—"Carpal Tunnel Syndrome: Correlations Between Pressure Measurement and Intraoperative Electrophysiological Nerve Study"—Muscle Nerve, 1990, vol. 13, pp. 1164-1168.

Agee, J. et al.—"Endoscopic release of the carpal tunnel: A randomized prospective multicenter study"—Journ. of Hand Surgery (American Volume), 1992, vol. 17A, pp. 987-995.
Al-Qattan, M.—"The Anatomical Site of Constriction of the Median Nerve in Patients with Severe Idiopathic Carpal Tunnel Syndrome"—Journ. of Hand Surgery (British and Euro. Volumes), 2006, vol. 31B, pp. 608-610.
Badalamente, M. et al.—"Enzyme Injection as Nonsurgical Treatment of Dupuytren's Disease"—Journ. of Hand Surgery, 2000, vol. 25A, pp. 629-636.
Badalamente, M. et al.—"Collagen as a Clinical Target: Nonoperative Treatment of Dupuytren's Disease"—Journ. of Hand Surgery, 2002, vol. 27A, pp. 788-798.
Badalamente, M. et al.—"Efficacy and Safety of Injectable Mixed Collagenase Subtypes in the Treatment of Dupuytren's Contracture"—Journ. of Hand Surgery, 2007, vol. 32A, pp. 767-774.
Cobb, T. et al.—"Anatomy of the flexor retinaculum"—Journ. of Hand Surgery (American Volume) , 1993, vol. 18A, pp. 91-99.
Cobb, T. et al.—"Effect of Lumbrical Muscle Incursion Within the Carpal Tunnel on Carpal Tunnel Pressure: A Cadaveric Study"—Journ. of Hand Surgery, 1995, vol. 20A, pp. 186-192.
Cobb, T. et al.—"Externally Applied Forces to the Palm Increase Carpal Tunnel Pressure"—Journ. of Hand Surgery (American Volume), 1995, vol. 20A, pp. 181-185.
Garcia-Elias, M. et al.—"Stability of the transverse carpal arch: an experimental study"—Journ. of Hand Surgery (American Volume), 1989, vol. 14A, p. 277-282.
Gelberman, R. et al.—"The carpal tunnel syndrome. A study of carpal canal pressures"—Journ. of Bone & Joint Surg., 1981, vol. 63, pp. 380-383.
Hamanaka, I. et al.—"Evaluation of Carpal Canal Pressure in Carpal Tunnel Syndrome"—Journ. of Hand Surgery (American Volume), 1995, vol. 20A, pp. 848-854.
Ikeda, K. et al.—"Segmental Carpal Canal Pressure in Patients with Carpal Tunnel Syndrome"—Journ. of Hand Surgery (American Volume), 2006, vol. 31A, pp. 925-929.
Keir, P. et al.—"The Effects of Tendon Load and Posture on Carpal Tunnel Pressure"—Journ. of Hand Surgery (American Volume), 1997, vol. 22A, pp. 628-634.
Keir, P. et al.—"Effects of Finger Posture on Carpal Tunnel Pressure During Wrist Motion"—Journ. of Hand Surgery (American Volume), 1998, vol. 23A, pp. 1004-1009.
Nakao, E. et al.—"Changes in Carpal Tunnel Pressures Following Endoscopic Carpal Tunnel Release: A Cadaveric Study"—Journ. of Hand Surgery (American Volume)—1998, vol. 23A, pp. 43-47.
Okutsu, I. et al.—"Measurement of pressure in the carpal canal before and after endoscopic management of carpal tunnel syndrome"—Journ. of Bone & Joint Surgery, 1989, vol. 71, pp. 679-683.
Rojviroj, S. et al.—"Pressures in the Carpal Tunnel: A Comparison Between Patients with Carpal Tunnel Syndrome and Normal Subjects"—Journ. of Bone & Joint Surgery, 1990, vol. 72B, pp. 516-518.
Sanz, J. et al.—"Postoperative Changes of Carpal Canal Pressure in Carpal Tunnel Syndrome: A Prospective Study with Follow-up of 1 Year"—Journ. of Hand Surgery (British Volume) , 2005, vol. 30B, pp. 611-614.
Schuind, F.—"Canal Pressures Before, During, and After Endoscopic Release for Idiopathic Carpal Tunnel Syndrome"—Journ. of Hand Surgery (American Volume), 2002, vol. 27A, pp. 1019-1025.
Seradge, H. et al.—"In Vivo Measurement of Carpal Tunnel Pressure in the Functioning Hand"—Journ. of Hand Surgery (American Volume), 1995, vol. 20A, pp. 855-859.
Szabo, R. et al.—"Stress carpal tunnel pressures in patients with carpal tunnel syndrome and normal patients"—Journ. of Hand Surgery (American Volume), 1989, vol. 14A, pp. 624-627.
Weiss, N. et al.—"Position of the wrist associated with the lowest carpal-tunnel pressure: implications for splint design"—Journ. of Bone & Joint Surgery, 1995, vol. 77, pp. 1695-1699.
Yii, N. et al.—"A Study of the Dynamic Relationship of the Lumbrical Muscles and the Carpal Tunnel"—Journ. of Hand Surgery (British and Euro. volume), 1994, vol. 19B, pp. 439-443.
Yoshida, A. et al.—"Is Complete Release of All Volar Carpal Canal Structures Necessary for Complete Decompression in Endoscopic

(56) References Cited

OTHER PUBLICATIONS

Carpal Tunnel Release?"—Journ. of Hand Surgery (European Volume), 2007, vol. 32E, pp. 537-542.

U.S. Appl. No. 60/927,437, filed May 3, 2007 in the name of Marie A. Badalamente.

International Search Report and Written Opinion from corresponding PCT International Patent Application No. PCT/US2010/028716, report issued on Jan. 6, 2011, pp. 1-20.

Watts, A.C. et al.—"The Use of a Fine-Gauge Needle to Reduce Pain in Open Carpal Tunnel Decompression: A Randomized Controlled Trial"—J. Hang Surg, vol. 30, No. 6, Sep. 2, 2005, pp. 615-617.

Lawrence, T.M. et al.—"Topical Anaesthesia to Reduce Pain Associated with Carpal Tunnel Surgery"—J. Hand Surg., vol. 27, No. 5, Oct. 2002, pp. 462-464.

Ozturk, K. et al.—"Comparison of carpal tunnel injection techniques: A cadaver study"—Scand. J. Plast. Reconstr. Surg. Hand Surg., vol. 42, 2008, pp. 300-304.

* cited by examiner

US 9,108,005 B2

TREATMENT OF CARPAL TUNNEL SYNDROME BY INJECTION OF THE FLEXOR RETINACULUM

CROSS-REFERENCE TO RELATED APPLICATIONS

This application is a divisional of U.S. patent application Ser. No. 12/732,047 filed on Mar. 25, 2010, now U.S. Pat. No. 8,702,654, incorporated herein by reference in its entirety, which in claims priority from U.S. provisional patent application Ser. No. 61/163,165 filed on Mar. 25, 2009, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL IN A COMPUTER PROGRAM APPENDIX

Not Applicable

BACKGROUND OF THE INVENTION

1. Field of the Invention

This invention pertains generally to treatment of carpal tunnel syndrome, and more particularly to both a method and apparatus for treatment by injection of a biological substance into the flexor retinaculum.

2. Description of Related Art

The carpal tunnel is an area in the hand adjacent the wrist which is formed by an arch of the eight wrist bones, spanned on its palmar surface by the flexor retinaculum. Functionally, the flexor retinaculum acts as a pulley. Passing through the carpal tunnel are nine flexor tendons with their synovial membranes, four lumbrical muscles, and median nerve. Without the flexor retinaculum, the flexor tendons tend to bowstring, losing their ability to preserve their appropriate moment arms, and resulting in a loss in both strength and dexterity to the wrist and hand that the carpal tunnel tendons help control.

Carpal tunnel syndrome (CTS) is a disease that refers to numerous clinical signs and symptoms resulting from an increase in pressure on the median nerve inside the carpal tunnel. The increased pressure compresses the median nerve, compromising its blood flow, resulting in the pain, numbness, and tingling characteristic of this disease. At present, it is the most widespread occupational health hazard in the industrial world. Billions of dollars are consumed each year in lost working time and in the diagnosis and treatment of this syndrome.

Intracarpal tunnel pressure is dynamic and influenced by numerous factors. Many of these factors have been studied previously, including disease, injury, wrist, position, hand use, compliance of the flexor retinaculumm, lumbrical muscles, externally applied force, and finger position. Not only does intracarpal tunnel pressure vary in response to these factors, but pressure dynamics also are determined by geometry of the carpal tunnel. Because of both the complex geometry and interaction among these factors, accurate measurement of intracarpal tunnel pressure remains difficult. In addition, pressure measurement is dependant on the type of measurement device used and whether introduction of the measurement device itself alters the pressure.

Active hand use produces the greatest range of pressures within the carpal tunnel. Most studies measuring intracarpal tunnel pressure during active hand use included patients with carpal tunnel syndrome (CTS). However, none of these studies quantified the hand use during pressure measurement. Because intracarpal tunnel pressure also is a function of location within the tunnel where pressure measurement is obtained, any characterization of the dynamics of intracarpal tunnel pressure should include a profile of pressure within the carpal canal. While others have identified the pressure profile that exists from proximal-to-distal within the carpal canal, only one of these included pressure measurements during active hand use. However, quantification of hand use was not reported.

Although the underlying cause of CTS is unknown, the treatment for CTS is well established. Non-operative treatments, including splinting, anti-inflammatory medications, and cortisone injections into the carpal tunnel, are often used initially to provide temporary relief of the symptoms. When non-operative treatments fail, the most effective treatment of CTS is surgical division of the flexor retinaculum. Surgical division of the flexor retinaculum causes a decrease in the pressure in the carpal tunnel allowing the return of normal blood flow to the median nerve, relieving the signs and symptoms of CTS. While various techniques exist for releasing the flexor retinaculum, the two most commonly used are open and endoscopic.

During an open release, a longitudinal incision is made through the skin in the palm of the hand and carried down through the subcutaneous fat, palmar fascia, palmaris brevis muscle, and finally through the flexor retinaculum. Once the flexor retinaculum is released, the skin is sutured and the wrist is frequently splinted until the wound heals. A typical surgery requires approximately 15 to 30 minutes and is performed as an outpatient procedure.

For an endoscopic release, various devices exist to perform incision of the flexor retinaculum. One device comprises a video endoscope and a hand piece that holds a disposable blade assembly. The device is inserted through a limited incision located in a wrist flexion crease. While viewing the deep side of the flexor retinaculum through a window located at the tip of the device, the blade is elevated to make the longitudinal incision while the device is withdrawn from the carpal tunnel. Next, the device is used to inspect the completeness of the incision through the flexor retinaculum and perform additional cutting if necessary. Once complete incision of the flexor retinaculum is achieved, the entry wound is sutured. The endoscopic release is performed as an outpatient procedure and requires approximately the same amount of time to perform as the open release.

Although complete surgical division of the flexor retinaculum is promoted as the standard of care in patients with CTS, there are a number of potential disadvantages associated with it, including:

(a) The arch formed by the carpal bones may be altered, affecting the functional biomechanics of the hand.

(b) The pulley effect created by the flexor retinaculum may be compromised and/or lost, allowing the digital flexor tendons and/or median nerve to sublux palmarwardly between the cut edges of the flexor retinaculum. Power grip and pinch are compromised until the flexor retinaculum heals adequately to re-establish the carpal tunnel as a competent pulley for the nine digital flexor tendons.

(c) Exposure of the cut edges of the flexor retinaculum permit scar tissue necessary for its healing in the lengthened position to be more abundant and therefore potentially creating greater post-operative morbidity, pain, and weakness.

(d) The length of time required for a patient to return to both their activities of daily living and work is affected by the trauma associated with a complete ligament division.

(e) The surgical techniques used require the expense of an operating room procedure rather than an office or clinic procedure.

(f) Following complete division of the flexor retinaculum, portions of the origins of the thenar and hypothenar muscle groups are unstable, causing pain and weakness of pinch and grip during the healing of the flexor retinaculum.

To avoid the potential disadvantages associated with current surgical techniques, an object of the present invention is a method and apparatus that weakens the structural integrity of the flexor retinaculum without using a surgical incision or surgically dividing portions or all of the flexor retinaculum. At least some of these objectives will be met in the following description.

BRIEF SUMMARY OF INVENTION

The present invention includes system and method to alter the stiffness of the flexor retinaculum so that it becomes more compliant, thereby causing the circumference of the carpal tunnel to expand and thus decrease the pressure on the contents of the carpal tunnel; similar to what occurs after surgical division of the flexor retinaculum. This allows the pressure within the carpal tunnel to return to an acceptable level, relieving the symptoms of CTS without a surgical operation.

According to an aspect of the invention, an apparatus and method is provided for identifying the flexor retinaculum of the carpal tunnel, injecting an effective amount of a drug either into any part of or adjacent to the flexor retinaculum (i.e. close enough to the flexor retinaculum so that the drug is effective), and increasing the tensile stress transmitted into the flexor retinaculum post-injection using hand exercises, thereby weakening its structural integrity and decreasing the pressure within the carpal tunnel that impairs median nerve function. In one embodiment, the apparatus comprises: (a) a drug with the ability to weaken the structural integrity of collagen; (b) an imaging detector for identifying the flexor retinaculum; (c) a detector frame configured to be coupled to the palm of the hand that both holds and positions the detector; (d) an injection needle with syringe for injecting the drug; and (e) a needle guide either attached to or integral with the imaging detector that holds, positions, and guides the injection needle.

Any drug that weakens the structural integrity of collagen may be used. In a preferred embodiment, collagenase may be used. Collagenase is an enzyme that has the affect of digesting collagen by breaking down the peptide bonds in the collagen protein.

The flexor retinaculum of the carpal tunnel comprises collagen fibers that are susceptible to breakdown by collagenase. Thus, the methods and systems of the present invention offer significant improvements over the current surgical methods by injecting collagenase either into any part of, or tissue adjacent to, the flexor retinaculum of the carpal tunnel, weakening the structural integrity of the collagen fibers, increasing the tensile stress in the flexor retinaculum, and causing the ligament to increase in length, thereby decreasing pressure on the median nerve and relieving the symptoms of CTS.

The present invention may include a combination of collagenase with a liquid carrier in an effective concentration for injection into or near the flexor retinaculum to weaken the structural integrity of collagen.

The "structural integrity" of collagen is herein defined as the ability of collagen to withstand tensile load. Once the structural integrity of collagen is weakened by collagenase, the threshold for tensile loading is lowered and the collagen fibers are no longer able to withstand the tensile loads that they could previous to the injection. Once tensile loads exceeding this lower threshold are applied to the collagen fibers, individual fibers fail structurally as a result of the broken bonds in the collagen protein. Initially, failure of the collagen fibers occurs on a microscopic level, progressing to complete failure of the collagen structure as the tensile load increases.

Direct injection of a drug into a part of or adjacent to the flexor retinaculum might be possible using only visual and palpation methods by a skilled physician knowledgeable of the anatomy of the hand. However, because the flexor retinaculum is deep to the palmar surface of the hand and neither visible nor palpable, an imaging means is desirable. In addition, to ensure that the drug dosage required to achieve the desired effect is accurately delivered at either a specific location or multiple locations either in or directly adjacent the flexor retinaculum, an imaging means is required for identifying the flexor retinaculum.

The imaging means can be any standard noninvasive imaging detector typically used for guiding injection needles. In the preferred embodiment, the imaging detector is an ultrasound transducer. Any standard commercially available ultrasound transducer with both hardware and software capabilities to produce high quality images of the anatomy of the wrist and hand can be used. While holding the imaging detector against the palmar skin and adjusting its position, the physician can observe on a display monitor acceptable images of both the flexor retinaculum and vital anatomic features that require avoidance during injection, including the median nerve, ulnar nerve, ulnar artery, and flexor tendons to the fingers. In addition, ultrasound can be used to identify the hook of the hamate, which is the anatomic attachment of the stiffest portion of the flexor retinaculum. It is at this location where the median nerve is the most compressed in the carpal tunnel. From the images, the flexor retinaculum can be both visually identified and its palmar-to-dorsal depth computed relative to a fixed reference position. In addition, having real-time images of the injection needle with respect to the anatomy of the carpal tunnel enables more accurate and repeatable injections of a drug at specific locations.

While holding and positioning the imaging detector can be performed manually by the physician, it is beneficial to have a detector frame that aids in this task. In the preferred embodiment, the detector frame is coupled to the patients hand. The detector frame both holds the imaging detector and provides both translational and rotational positioning of the imaging detector on the palm of the patient's hand. Use of a detector frame enables more freedom of the physician's hands, ensures stable images of the desired anatomy, and provides a stable reference frame from which an injection needle can be guided.

With the flexor retinaculum both identified and its depth known relative to the palmar skin, an injection needle can be guided to it. Any standard commercially available hypodermic needle of suitable length and diameter and syringe (or equivalent means for containing the drug to be injected) of appropriate sizes can be used to dispense an effective amount (dose) of drug. Using either visual guidance provided by the ultrasonic images or depth information computed from the ultrasound, the tip of the injection needle can be inserted either into a specific segment of or adjacent to the flexor retinaculum.

While holding, positioning, and guiding the injection needle can be performed manually by the physician, it is beneficial to use a needle guide that aids in this task. In the preferred embodiment, a needle guide attaches to the imaging detector and holds the injection needle, positions it at both the desired angle and location for entry into the skin, and guides the needle, as it is advanced by the physician, along a trajectory that ensures insertion of the tip of the needle at the desired location either into or adjacent the flexor retinaculum. Once at the desired location, the physician can dispense an effective dosage of the drug.

After deposition of the drug either into a part of or adjacent to the flexor retinaculum, it may be necessary, once the structural integrity of the collagen fibers have weakened, for the patient to actively increase the magnitude of tensile stress in the flexor retinaculum. The resulting increase in tensile stress in the weakened collagen fibers will cause them to either abruptly fail or increase in anatomic length over time. To provide the necessary increase in tensile stress in the weakened collagen fibers, the physician may prescribe a hand exercise routine.

Accordingly, an aspect of the present invention is a method for treating a patient with carpal tunnel syndrome, comprising: identifying a location of the patient's flexor retinaculum suitable for treatment; and injecting an agent into said location of the flexor retinaculum in one or more doses sufficient to weaken the structural integrity of the flexor retinaculum.

In one embodiment, the flexor retinaculum includes the transverse carpal ligament and/or its attachment to the bones.

In another embodiment, the agent comprises: one or more doses of collagenase, a corticosteroid, or both.

In a further embodiment, identifying a suitable treatment location of the patient's flexor retinaculum comprises: positioning an imaging detector adjacent a region of the patient's hand; the region being associated with the flexor retinaculum, and generating an image of the patient's hand. The imaging detector may comprise ultrasound imaging, X-ray imaging, Magnetic Resonance Imaging, or the like.

In one mode of the current embodiment, generating an image comprises positioning an ultrasound transducer adjacent the patient's hand and generating an ultrasound image.

In another embodiment, the method further includes increasing the tensile stress in the flexor retinaculum subsequent to injecting said agent. The increase in tensile stress may be generated by pressure within the carpal tunnel, said pressure generated by one or more of the following: having the patient use one or more digits of the hand, having the patient grip the hand around an object; flexing one or more fingers into the palm of the hand and having the patient pinch a thumb and one or more fingers of the hand together. The object may comprise a dynamometer, and be pressed into the palm or heel of the patient's hand.

In yet another embodiment, the method includes measuring pressure within the carpal tunnel In addition to the injection of an agent, the method may include cutting the flexor retinaculum with a blade.

In one embodiment, identifying a suitable treatment location of the patient's flexor retinaculum further comprises computing the palmar-to-dorsal depth from the palm of the hand to the flexor retinaculum; wherein the agent is injected via a needle at said computed palmer-to-dorsal depth along an axis substantially parallel to an imaging surface of the detector, or a longitudinal axis of the flexor retinaculum.

In another embodiment, the agent is delivered at a central portion of the flexor retinaculum.

In a further embodiment, the method may include inserting a guide tube into the hand adjacent the flexor retinaculum; and accessing the flexor retinaculum at the distal end of the guide tube. In the current mode, the method may include advancing a pressure sensor within said guide tube to said treatment location, and measuring the pressure at said location. In addition, the method may include advancing a cutting probe within said guide tube to said treatment location; and cutting tissue associated with the flexor retinaculum.

Another aspect is a system for treating a patient with carpal tunnel syndrome, comprising: a needle guide; an injection needle; the needle guide comprising a guide hole configured for receiving the injection needle; and an agent configured for delivery within said injection needle to a tissue region associated with the flexor retinaculum of the patient; wherein said agent is configured to weaken the structural integrity of the flexor retinaculum.

In one embodiment, the system includes a clamp coupled to the needle guide; wherein the clamp comprises a reference surface for positioning at a palm of the patient's hand; wherein the needle guide is slideably coupled to the clamp such that the needle guide may be adjusted with respect to the reference surface. In a preferred mode, the longitudinal axis of the guide hole is substantially parallel to the reference surface.

In another mode of the current embodiment, the system comprises an imaging device configured for imaging the carpal tunnel during injection; wherein the clamp is configured to house the imaging device. The imaging device may be pivotably coupled to the clamp to allow for transverse and longitudinal images of the carpal tunnel to be obtained.

In another mode, the imaging device comprises an imaging surface; wherein the imaging surface is substantially parallel to the longitudinal axis of the guide hole of the needle guide. The needle guide may be configured to be adjusted in a palmar-dorsal direction while the guide hole remains substantially parallel to the imaging surface. The clamp and needle guide may comprise an indicator configured to indicate a depth of needle insertion with respect to the reference surface.

In another embodiment, the system includes a guide tube disposed within the guide hole; the guide tube configured to be inserted into the hand adjacent the flexor retinaculum; wherein the guide tube comprises a central channel sized to accommodate delivery of an instrument to the tissue region. The delivery instrument may comprise a pressure sensor sized to be received within said guide tube to be delivered to the tissue region; wherein the pressure sensor is configured to measuring the pressure at said location, or a cutting probe sized to be received within said guide tube to be delivered to the tissue region; and the cutting probe configured to cut tissue associated with the flexor retinaculum.

In another embodiment, a linkage is attached to the clamp; wherein the linkage is configured to secure to the patients hand; wherein the linkage comprises a first joint that allows rotation of the clamp with respect to the hand. The first joint is configured to allow rotation of the clamp in a flexion-extension direction with respect to the patient's hand. The linkage may further include a second joint; wherein the second joint is configured to allow rotation of the clamp in a radial-ulnar direction with respect to the patient's hand.

In another embodiment, the linkage system provides translational and rotational adjustments of the imaging detector and needle/probe guide relative to the patient's hand. In one mode of the current embodiment, the linkage system establishes a fixed point distal to the imaging detector about which the longitudinal axis of a contact line between a patient's ring and long fingers always intersects.

Another aspect is an apparatus for treating a patient with carpal tunnel syndrome, comprising: a needle guide; an injection needle; the needle guide comprising a guide hole configured for receiving the injection needle; a clamp coupled to the needle guide; wherein the clamp comprises a reference surface for positioning at a palm of the patient's hand; wherein the needle guide is slideably coupled to the clamp such that the needle guide may be adjusted with respect to the reference surface; and an imaging device configured for imaging the carpal tunnel during injection; wherein the clamp is configured to house the imaging device.

The apparatus preferably includes an agent configured for delivery within said injection needle to a tissue region associated with the flexor retinaculum of the patient; wherein said agent is configured to weaken the structural integrity of the flexor retinaculum. Preferably, the guide hole is substantially parallel to the reference surface.

In one embodiment, the apparatus further comprises a linkage attached to the clamp; wherein the linkage is configured to secure to the patients hand and has first and second joints that allow rotation of the clamp with respect to the hand; wherein the first joint is configured to allow rotation of the clamp in a flexion-extension direction with respect to the patient's hand; and wherein the second joint is configured to allow rotation of the clamp in a radial-ulnar direction with respect to the patient's hand.

Another aspect is an apparatus for treating a patient with carpal tunnel syndrome, comprising: a base configured to support a patient's forearm and hand; the base comprising a first surface configured to support the forearm and a second surface configured to support the hand; wherein the second surface is adjacent to the first surface and disposed at an angle with the first surface; a pivotable arm coupled to the base; wherein the pivotable arm is configured to support a needle guide; the needle guide comprising a guide hole configured for receiving the injection needle; and a clamp coupling the pivotable arm and the needle guide; wherein the needle guide is slideably coupled to the clamp such that the needle guide may be adjusted with respect to the second surface.

In a preferred embodiment, the apparatus includes an agent configured for delivery within said injection needle to a tissue region associated with the flexor retinaculum of the patient; wherein said agent is configured to weaken the structural integrity of the flexor retinaculum.

In another embodiment, the apparatus includes an imaging device configured for imaging the carpal tunnel during injection, wherein the clamp is configured to house the imaging device.

In yet another embodiment, the guide hole is substantially parallel to the second surface, and the needle guide is configured to be adjusted in a palmar-dorsal direction while the guide hole remains substantially parallel to the second surface. The clamp and needle guide comprise an indicator configured to indicate a depth of needle insertion with respect to the reference surface. Furthermore, the pivotable arm allows translation and rotation of the needle guide with respect to the second surface.

Another aspect of the invention is a method for treating a patient with carpal tunnel syndrome, comprising: injecting a drug into or adjacent to the flexor retinaculum in one or more doses sufficient to weaken the structural integrity of the flexor retinaculum: and increasing the tensile stress in the flexor retinaculum. The pressure within the carpal tunnel may also be measured. Additionally, the flexor retinaculum may be cut with a blade and using an imaging method to display the flexor retinaculum on a monitor while cutting.

Another aspect of the invention is a percutaneous injection device for use with a medical imaging detector, comprising: a clamp configured for attachment to the imaging detector; a needle guide configured for attachment to the clamp and which is adjustable along an axis that is substantially parallel to the longitudinal axis of the imaging detector; and an injection needle configured for insertion through the needle guide; the injection needle having a longitudinal axis substantially parallel to the imaging surface of the imaging detector when inserted through the needle guide.

Another aspect of the invention is a system for treating a patient with carpal tunnel syndrome, comprising: an imaging detector; a clamp that couples to the imaging detector; a guide that attaches to the clamp and is adjustable along an axis that is substantially parallel to the longitudinal axis of the imaging detector; a probe with a cutting blade whose long axis is substantially parallel to the imaging surface of the imaging detector when inserted through the guide; and a pressure measurement device for measuring pressure within the carpal tunnel.

Another aspect of the invention is a device for a medical imaging detector, comprising: a clamp configured to attach to the imaging detector; a probe guide configured to attach to the clamp and which is adjustable along an axis that is substantially parallel to the longitudinal axis of the imaging detector; a probe with a cutting blade whose long axis is substantially parallel to the imaging surface of the imaging detector when inserted through the probe guide; and a linkage system attached to the clamp that attaches to the patient's hand.

Another aspect of the invention is a system for treating a patient with carpal tunnel syndrome, comprising: an imaging detector; a guide that is integral with the imaging detector and is adjustable along an axis that is substantially parallel to the longitudinal axis of the imaging detector; and a probe with a cutting blade whose longitudinal axis is substantially parallel to the imaging surface of the imaging detector when inserted through the guide.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF INVENTION

Figure 1:
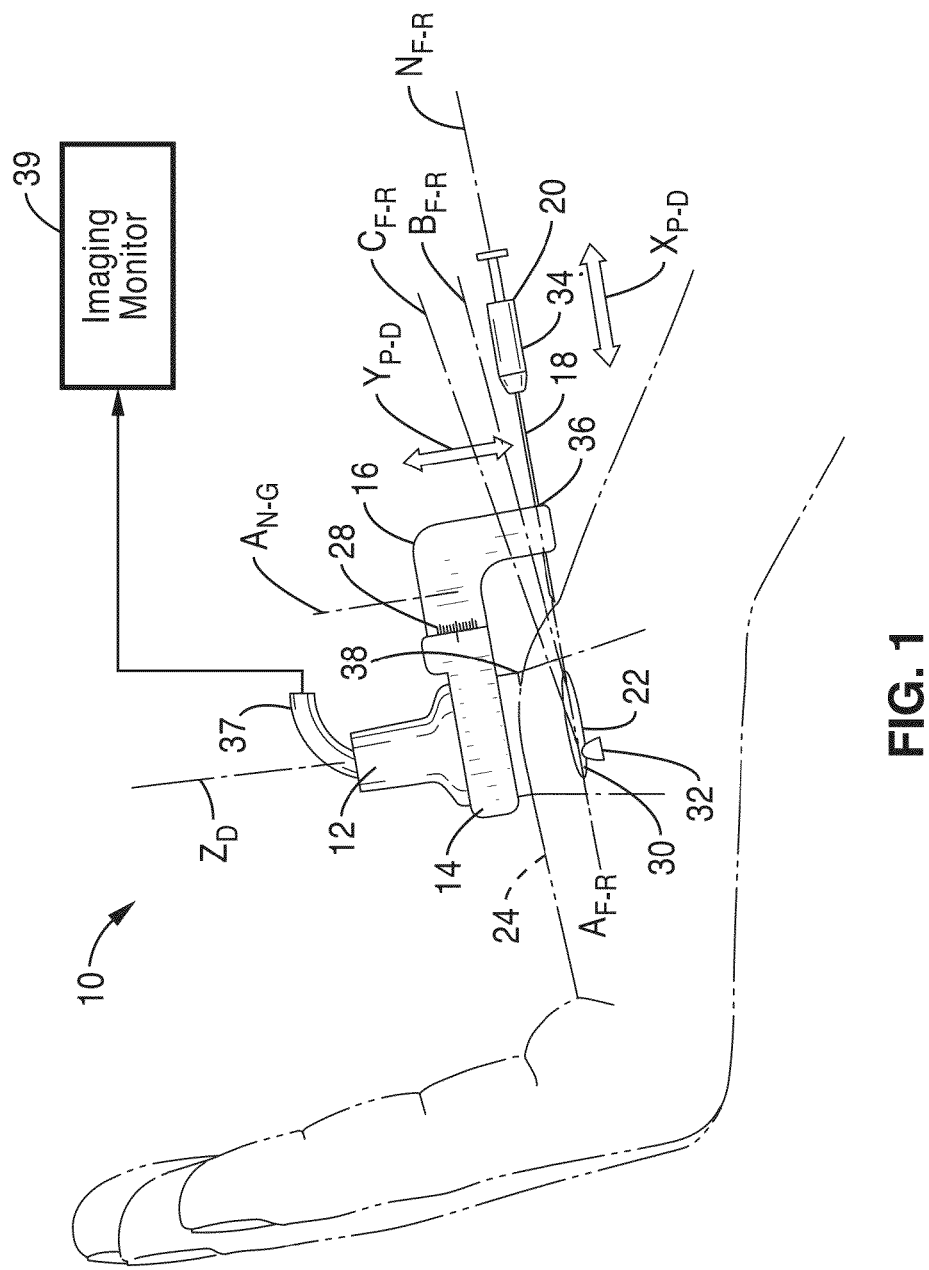
FIG. 1 is a perspective view of an embodiment of an injection apparatus according to the present invention, with the imaging detector positioned parallel to the imaged anatomy.

Referring more specifically to the drawings, for illustrative purposes the present invention is embodied in the apparatus generally shown in FIG. 1 through FIG. 20. It will be appreciated that the apparatus may vary as to configuration and as to details of the parts, and that the method may vary as to the specific steps and sequence, without departing from the basic concepts as disclosed herein.

FIGS. 1-20 detail methods and apparatus for injecting an agent or drug into at least a part of the flexor retinaculum, or tissue adjacent thereto, to treat and relieve the symptoms of CTS. One aspect is injection of a drug in a dose that can sufficiently weaken the structural integrity of the collagen fibers that form the flexor retinaculum. The second aspect is to induce sufficient tensile stress in the weakened collagen fibers so that they either rupture or their length increases as a result of fiber growth over time.

In a preferred embodiment, an agent containing collagenase is used for weakening the structural integrity of collagen fibers. Collagenase is produced naturally by the body and is essential for the normal remodeling of tissues composed of collagen. In particular, an injectable form of collagenase, clostridium histolyticum (Xiaflex), is injected in or near the flexor retinaculum.

The dosage amount and concentration of collagenase used for treatment of CTS may comprise a single injection of up to 0.9 mg of collagenase, wherein the total volume of the concentration injected is less than 0.5 ml. If a single injection does not weaken the collagen adequately to enable failure of the fibrous cords, up to four additional injections of up to 0.9 mg may be performed.

Alternatively, corticosteroids or any other drug that weakens the structural integrity of collagen may be used. While injections of corticosteroids provide temporary relief of the symptoms in patients with CTS, the drug is typically injected into the synovium that surrounds the contents of the carpal tunnel, not into or directly adjacent the flexor retinaculum as provided in the system of the present invention.

In other areas of the body where corticosteroids are used for the treatment of painful soft tissue injuries (tennis elbow, medial epicondylitis, achilles tendonitis and plantar fasciitis), the corticosteroid frequently weakens the collagen fibers of the tendon or ligament after multiple injections. This results in a sudden rupture of the tendon, either along its length or at its origin or insertion into bone, when tensile load from active muscle use is applied to the weakened collagen fibers. The various corticosteroids, their dosage amounts and concentrations typically used for the treatment of these painful soft tissue injuries would be effective for injecting either into any part of or adjacent to the flexor retinaculum, particularly adjacent to the palmar side, to weaken the structural integrity of its collagen fibers In one embodiment, an agent comprising a combination of collagenase and corticosteroids is injected at or near the flexor retinaculum for the treatment of patients with CTS. Because of the anti-inflammatory effect of corticosteroids, a combination of corticosteroid with collagenase may provide improved relief of symptoms. One of the known adverse reactions from a collagenase injection is inflammation. A corticosteroid may be either mixed together with the collagenase in the same dose that is injected into the flexor retinaculum or injected separately from the collagenase injection. If the corticosteroid is injected separately, it may be injected either prior to, at the same time as, or subsequent to the collagenase injection. A corticosteroid injected separately may be administered either into the carpal tunnel synovium, into any part of the flexor retinaculum or adjacent the flexor retinaculum.

In another embodiment, the injection of a corticosteroid, collagenase or other agent may be deposited into the synovium that surrounds the contents of the carpal tunnel. In this case, the intent is not to weaken the structural integrity of the flexor retinaculum, but is to relieve the symptoms of carpal tunnel syndrome; similar to what a standard steroid injection does now.

The present invention details an injection/agent delivery device to aid with safely and accurately injecting an agent as described above at desired locations either into or directly adjacent the flexor retinaculum. FIG. 1 shows one embodiment of an injection device 10 according to the invention for both identifying the flexor retinaculum of the carpal tunnel using ultrasound imaging and injecting a drug into any part of or adjacent to the flexor retinaculum. In the embodiment shown, injection device 10 comprises an imaging detector 12 held in a clamp 14, a needle guide 16, and an injection needle 18 with its attached syringe 20 containing the drug 34.

The imaging means 12 can be any standard noninvasive imaging detector typically used for guiding injection needles. In the preferred embodiment, the imaging detector 12 is a standard commercially available ultrasound transducer connected via cable 37 to an ultrasound imaging monitor 39 having both hardware and software capable of producing high quality images of the flexor retinaculum 22 and other associated anatomy of the wrist and hand. In a standard ultrasound system, the image monitor 39 is remote from the imaging detector 12. To facilitate the procedure of injecting while imaging, it may be advantageous to locate the image monitor 39 adjacent the hand that is being imaged.

While holding the imaging detector 12 against the palmar skin 24 and adjusting its position, the physician can observe on a display monitor acceptable images of both the flexor retinaculum 22 and vital anatomic features that require avoidance during injection, including the median nerve, ulnar nerve, ulnar artery, and flexor tendons to the fingers. In addition, ultrasound can be used to identify the hook of the hamate 32, which is the anatomic attachment of the stiffest portion of the flexor retinaculum. It is at this location where the median nerve is the most compressed in the carpal tunnel. From the images, the flexor retinaculum 22 can be both visually identified and its palmar-to-dorsal depth computed relative to a fixed reference position. In addition, having real-time images of the injection needle with respect to the anatomy of the carpal tunnel enables more accurate and repeatable injections of a drug at specific locations.

Other standard commercially available imaging devices such as MRI, X-ray, or the like, may be used for imaging the hand during the procedure to facilitate guidance of the injection needle 18. However, ultrasound imaging offers certain advantages, including real-time images of the flexor retinaculum 22 as the injection needle 18 and drug 34 are deployed into it and no radiation exposure to the patient. It is also appreciated that the needle guide 16 may be made integral with the housing of the imaging detector 12.

Figure 2:
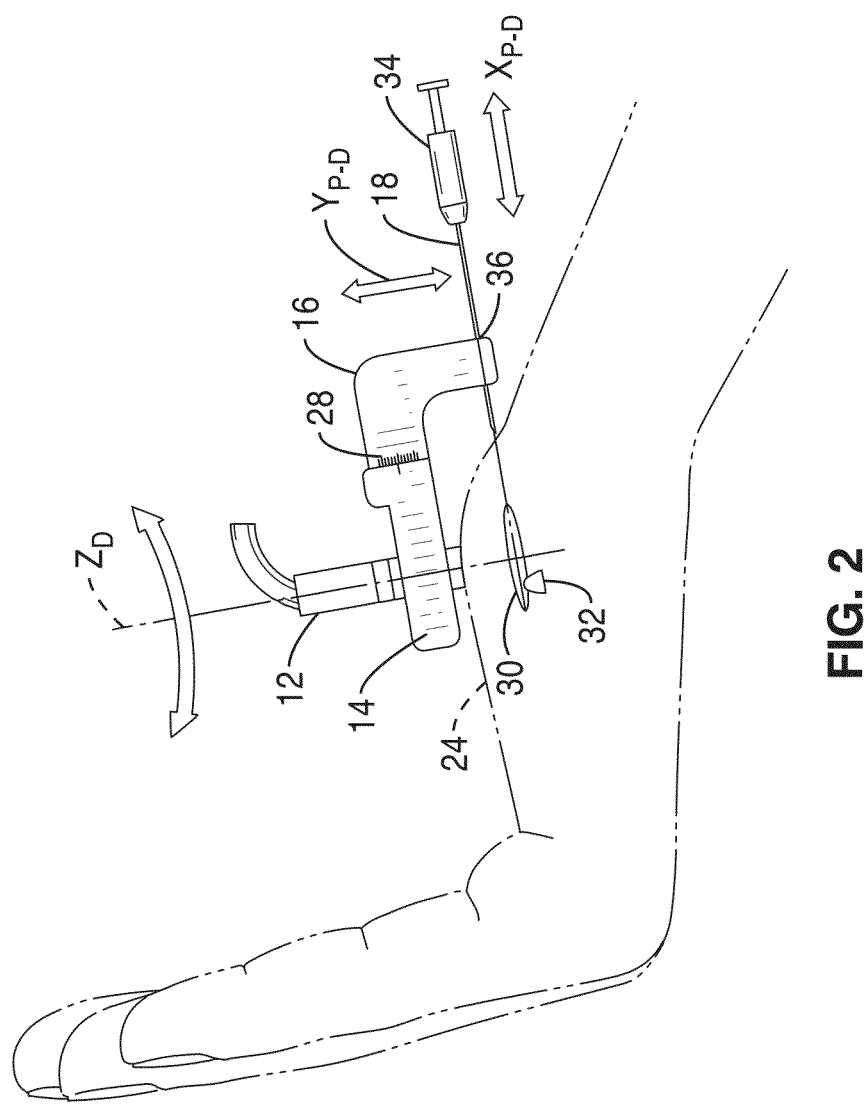
FIG. 2 is a perspective view of an embodiment of an injection apparatus according to the present invention with the imaging detector positioned transverse to the imaged anatomy.

With the injection device 10 held by the physician, the imaging surface 38 of the imaging detector 12 can be positioned on the palm of the patient's hand 24 either longitudinally, as shown in FIG. 1, or rotated 90 degrees about the longitudinal axis of the imaging detector $Z_D$ to a transverse position, as shown in FIG. 2.

Alternatively, two imaging detectors (not shown) may be either contained in a single clamp 14, or held separately, one oriented to provide a longitudinal image and the other oriented to provide a transverse image of the patient's carpal tunnel anatomy. The two imaging detectors could be either identical, or have differing physical dimensions and/or performance capabilities. Using this arrangement, two images of the carpal tunnel anatomy may be displayed simultaneously on the image monitor.

In an alternative embodiment, a single imaging detector 12 can be used with software (not shown) in the image monitor 39 that has the capability of providing three-dimensional images using either mechanical or electronic switching that scans using both longitudinal and transverse imaging.

To both enhance the acoustic quality of the ultrasound signals and enable ease of positioning the imaging detector 12, a standard commercially available aqueous ultrasound gel, or other suitable material for conducting sound, is applied to the palm of the patient's hand 24 prior to imaging. When the desired image of the flexor retinaculum 22 is obtained, the needle guide 16 is adjusted in a palmar-dorsal direction $Y_{P-D}$, along the axis of adjustment of the needle guide $A_{N-G}$, to align the injection needle 18 with the desired location for injection. The axis along which the needle guide is adjusted $A_{N-G}$ is parallel to the longitudinal axis of the imaging detector $Z_D$.

Needle guide 16 is slideably coupled to clamp 14 via a dovetail joint 35 (see FIG. 5) that allows controlled translation of the needle guide 16 with respect to the clamp 14 in only the $Y_{P-D}$ direction. Ultrasound depth information displayed on the image monitor is used to compute the palmar-dorsal depth from the palm of the hand 24 to the flexor retinaculum 22. The desired depth is set using the indicator marks 28 (comprising increments in either mm or inches), which reference the palmar-dorsal position of the needle guide 16 to the clamp 14.

It is appreciated that surface 38 may comprise a surface of the detector 12, or the clamp 14 housing the detector 12. In one embodiment, the device 10 may not have a detector 12. In this mode, the clamp 14 merely acts as a housing or base that provides a reference surface 38 to rest the device 10 on the palm 24 of the hand. Anatomical measurements and or imaging of the patient may previously be conducted (e.g. via a pre-op diagnostic or the like procedure), such that the physician sets the desired depth in the palmar-dorsal direction $Y_{P-D}$ and advances the needle 18 to the desired treatment location.

Having the patient flex and extend their fingers during imaging may be used to highlight the contrast between the mobile flexor tendons and the static flexor retinaculum, enabling better identification of the dorsal margin of the flexor retinaculum.

With the needle guide 16 set to the desired position, and the patient's wrist held in some appropriate degree of extension, the physician advances the injection needle 18 along a proximal-to-distal direction $X_{P-D}$ through the guide aperture 36. The long axis $N_{F-R}$ of hole 36 is preferably parallel with the imaging surface 38 of the imaging detector 12, so that the needle 18 enters the patient's skin proximal to the distal wrist crease and is advanced until the needle's tip reaches the desired treatment location. Advancement of the needle's shaft 18 is displayed on the imaging monitor 39 via detector 12. Under image guidance, the injection needle 18 enters the flexor retinaculum 22 along its longitudinal axis $A_{FR}$.

The longitudinal axis $A_{F-R}$ of the flexor retinaculum 22 is defined as an axis that extends from proximal to distal, intersecting generally perpendicular to the distal edge of the flexor retinaculum 22. To prevent soft tissue from entering the bore of the injection needle 18 during insertion and causing blockage of the injection needle 18, a standard commercially available removable stylet that fits within the bore can be used and then removed prior to dispensing the drug 34.

As shown in FIG. 1, the imaging surface 38 of the imaging detector 12 (and needle aperture axis $N_{F-R}$) is positioned by the physician to be parallel with the longitudinal axis of the flexor retinaculum $A_{F-R}$. This is preferably indicated on the imaging monitor 39 as being parallel with either the upper or lower edge of the monitor screen (not shown). In this position, the long axis $N_{F-R}$ of the injection needle 18 is coincident with the longitudinal axis $A_{FR}$ of the flexor retinaculum 22, entering it at its proximal extent, and is advanced distally with the drug 34 deposited at either a single or multiple locations.

Flow of the drug 34 from the syringe 20 into the flexor retinaculum 22 may be readily observed visually on the imaging monitor 39. If additional enhancement of the flow dynamics of the drug 34 is desired, commercially available microspheres or any other commercially available image-enhancement particles may be added to the drug 34 prior to injection.

A number of target locations for injection may be advantageous. One injection location is where the flexor retinaculum 22 is stiffest and therefore, its structural integrity requires more substantial weakening of its tensile strength. The transverse stiffness of the flexor retinaculum 22 varies from the proximal to distal borders of the carpal tunnel. The stiffness of the ligament is generally the stiffest at a location within the central portion of the flexor retinaculum 22, called the transverse carpal ligament 30. This location, where the ligament also is the thickest, coincides with the transverse carpal ligament's attachment between the hook of the hamate bone 32 and the ridge of the trapezium bone. In addition, it is at this location within the carpal tunnel where the pressures on the median nerve are the greatest. Imaging can be used to both identify the transverse carpal ligament 30 and precisely guide the injection needle 18 into it. Another location requiring precise image-guided injection is where the transverse carpal ligament 30 attaches to the bones of either the hook of the hamate bone 32 or the trapezium bone (not shown). At this location, the collagen fibers blend into bone, making the ligament stiffer.

Another location for injection requiring precise image guidance includes into the flexor retinaculum directly palmar to the median nerve.

If a sufficient amount of drug 34 cannot be injected into the flexor retinaculum 22, the drug 34 may be injected directly adjacent the flexor retinaculum 22. Using the depth information from the ultrasound, the needle guide 16 is preferably positioned in the palmar-dorsal direction $Y_{P-D}$, along the axis of adjustment of the needle guide $A_{N-G}$, prior to insertion of the injection needle 18 so that the injection needle 18 is either more palmar or dorsal to the flexor retinaculum 22. Under image guidance, the injection needle 18 may be inserted and precisely placed adjacent the ligament, either palmar or dorsal, and the drug 34 deposited. Locations that may be advantageous for deposition of the drug include adjacent to the flexor retinaculum directly palmar to the median nerve, adjacent to the flexor retinaculum within the carpal tunnel, adjacent to the flexor retinaculum within the carpal tunnel adjacent the median nerve, and adjacent to the flexor retinaculum within the carpal tunnel ulnar to the median nerve. Diffusion of the drug 34 into the flexor retinaculum 22 is sufficient to cause weakening of the collagen fibers.

In the embodiment of the invention shown in FIG. 1, the longitudinal axis $N_{F-R}$ of the guide hole 36 is perpendicular to the axis of adjustment $A_{N-G}$ of the needle guide 16. Alternatively, the guide hole 36 can traverse the needle guide 16 at an angle so that when the injection needle 18 is inserted through the guide hole 36, it intersects the flexor retinaculum 22 at an acute angle. FIG. 1 shows two examples of alternative guide hole 36 locations that enable insertion of the injection needle 18 along axes $B_{F-R}$ & $C_{F-R}$ that aim toward the flexor retinaculum 22, but are not in the proximal-to-distal direction $X_{P-D}$. With these alternative guide hole 36 locations, the injection needle 18 may enter the patient's skin distal to the distal wrist crease. Additional locations of the guide hole 36 in the needle guide 16 also are possible.

By using one of these alternative placements of the guide hole 36 in the needle guide 16, various additional attachment positions of the needle guide 16 to the clamp 14 may be used. In FIG. 1 the needle guide 16 is attached to the clamp 14 on its proximal end. Alternatively, the needle guide 16 could be attached on the radial, ulnar, or distal sides of the clamp 14. By using these alternative positions, the injection needle 18 can be inserted either into any part of or adjacent to the flexor retinaculum 22 using image guidance as the injection needle 18 enters the field of view.

Figure 3:
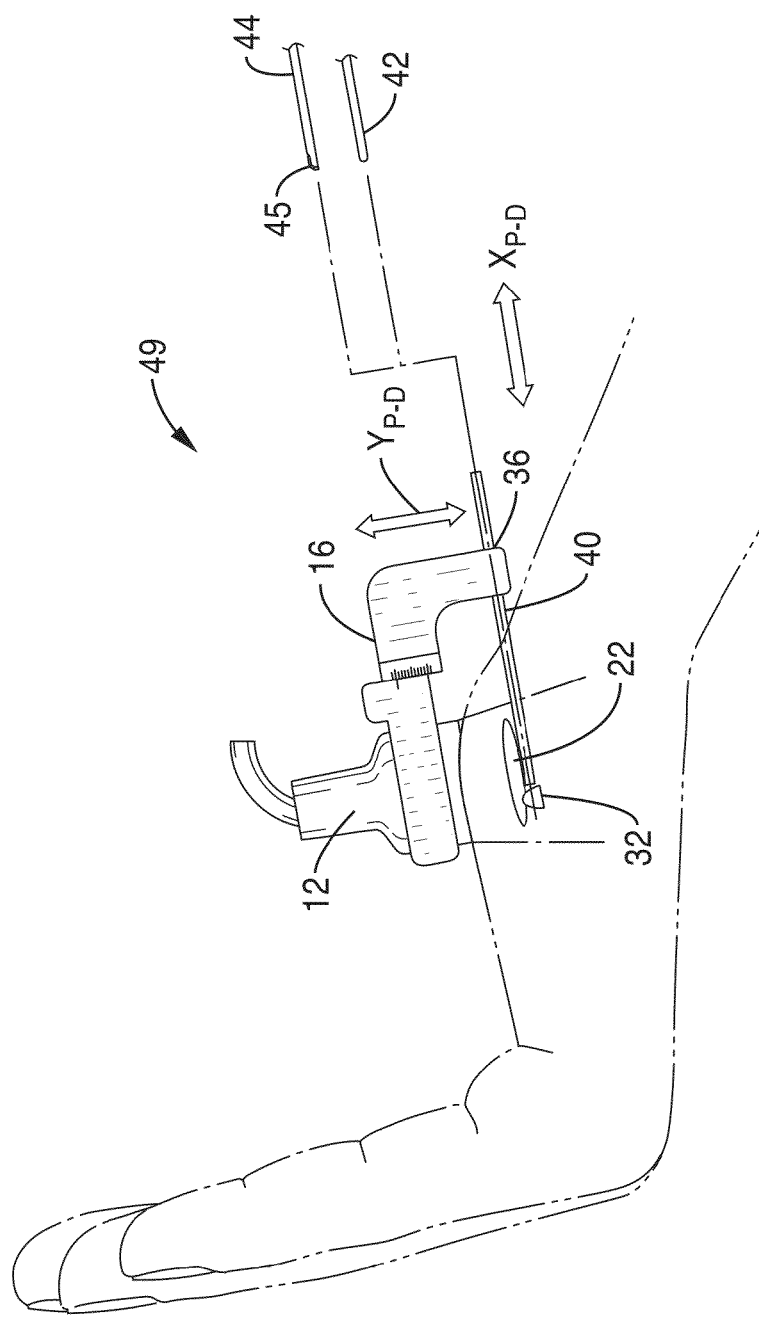
FIG. 3 is a perspective view of an embodiment of an injection apparatus according to the present invention similar to that shown in FIG. 1, but with the injection needle replaced with alternative devices for measurement and treatment of carpal tunnel syndrome.

FIG. 3 shows an injection device 49 with a guide tube 40 inserted into the carpal tunnel dorsal to the flexor retinaculum 22. Using the same method described for insertion of an injection needle, the needle guide/adjuster 16 is positioned in a palmar-dorsal direction $Y_{P-D}$ to obtain the desired entry location of the guide tube 40. Needle guide has an expanded bore 36 for accommodating the guide tube 40. The guide tube 40 is inserted as a conduit for alternative measurement and treatment techniques that are used either in combination with an injection of the flexor retinaculum 22 or as separate procedures. One alternative is a diagnostic measurement of the carpal tunnel pressure using a standard commercially available pressure sensor 42. Either prior to or following treatment to the flexor retinaculum 22 with a drug, the pressure sensor 42 is inserted through the guide tube 40 into the carpal tunnel where the pressure is measured. Because the greatest pressure has been shown to occur both adjacent the dorsal surface of the flexor retinaculum 22 and adjacent the hook of the hamate 32, it is desirable to measure the pressure in this location. The use of the imaging detector 12 can both aid and confirm placement of the pressure sensor 42 at this location.

In another embodiment, the guide tube 40 is configured to direct positioning of a cutting probe 44 to the treatment location. Cutting probe 44 may comprise a cutting blade 45, or may comprise a standard hypodermic needle with the bevel on the needle acting as a cutting blade. Cutting may be used to either create a space adjacent to the flexor retinaculum or create a separation in the fibers of the flexor retinaculum to enhance the ability of the flexor retinaculum to absorb the delivered drug or agent. Guide tube 40 may be used to position needle 18 in a similar manner for drug delivery to the desired treatment site. In addition, cutting of the fibers of the flexor retinaculum will weaken the segment of the ligament receiving the injection. The cutting probe 44 may also be used to perform division of the flexor retinaculum 22.

Figure 4:
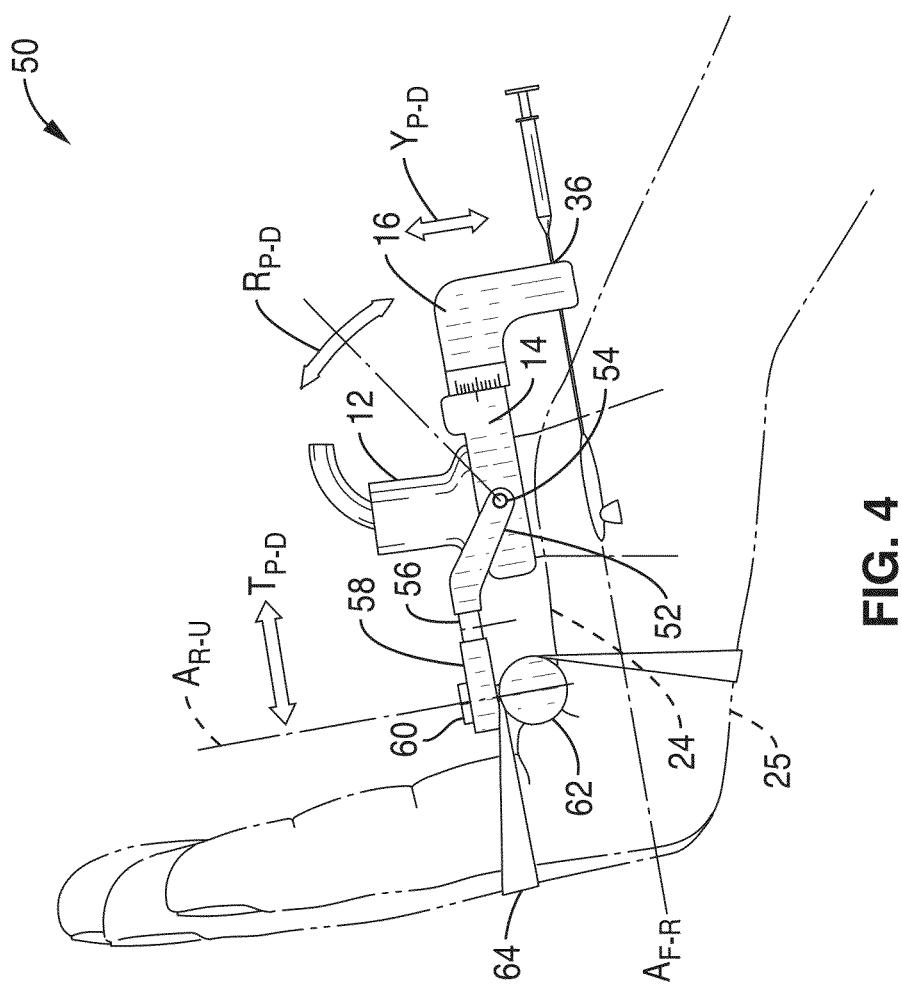
FIG. 4 is a perspective view of an embodiment of an injection apparatus according to the present invention shown secured to the hand.

FIG. 4 shows another embodiment of an injection device 50 according to the invention for both identifying the flexor retinaculum of the carpal tunnel and injecting a drug into any part of the flexor retinaculum or adjacent tissue region. The injection device 50 shown in FIG. 4 is similar to that shown in FIG. 1, but utilizes an additional attachment means for both aligning and supporting the imaging detector 12 and needle guide 16 on the patient's hand.

Both rotational and translational alignment of the imaging detector 12 shown in FIG. 1 are performed manually by the physician as he/she holds the imaging detector 12 and positions it to obtain optimal images of the desired anatomy. This requires the physician to hold the imaging detector 12 while trying to keep both the desired image and correct orientation of the needle guide 16. The injection device 50 shown in FIG. 4 provides the same rotational and translational alignments of the image detector 12 and needle guide 16, but maintains both support and alignment of the imaging detector 12 when the physician releases their hold of the image detector 12.

Figure 5:
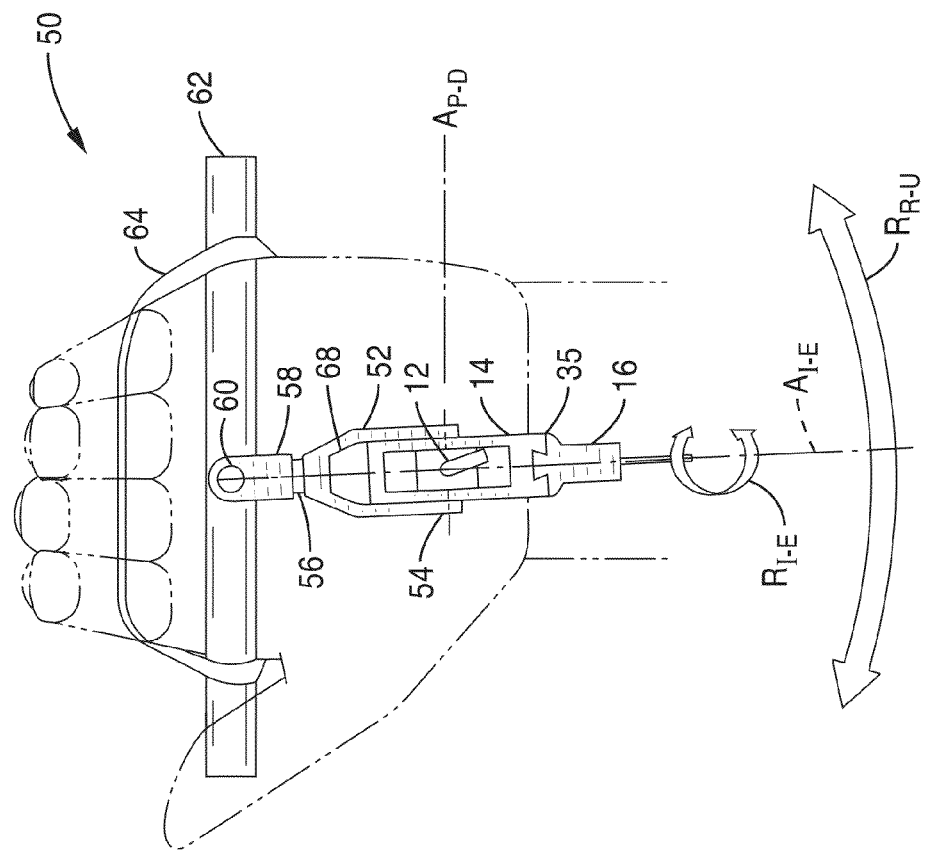
FIG. 5 is an anterior-posterior view of the injection apparatus shown in FIG. 4.

Clamp 14 secures the imaging detector 12, and is attached to a clevis 52 having opening 68 via a pin 54. Attachment is facilitated using a pin 54 to enable rotation of the clamp 14 in a palmar-dorsal direction $R_{P-D}$ about the longitudinal axis $A_{PD}$ of the pin 54 as shown in FIG. 5. On the opposite end of the clevis 52 is a link 56 that slides into both the clevis 52 and a pivot joint housing 58. Link 56 permits both translation between the clevis 52 and pivot joint housing 58 in a proximal-to-distal direction $T_{P-D}$ and rotation in an internal-external direction $R_{I-E}$ about the longitudinal axis $A_{IE}$ of the link 56 as shown in FIG. 5. A hole in the distal end of the pivot joint housing 58 slides onto a pivot pin 60. Pivot pin 60 provides rotation of the injection device 50 in the radial-ulnar direction $R_{R-U}$ about the longitudinal axis $A_{RU}$ of the pivot pin 60 as shown in FIG. 5. By having this rotational adjustability, the imaging detector can be positioned to both view the critical anatomy that is of interest from radial to ulnar, including the hook of the hamate, ulnar artery, and ulnar nerve, and identify a safe path for the injection needle.

The opposite end of the pivot pin 60 inserts into a rod 62 that is configured to be placed in the palm of the patient's hand 24 adjacent the metacarpophalangeal joints of the fingers. To secure the rod 62 to the patient's hand, an elastic band 64 is wrapped around each end of the rod 62 and then around both the dorsal sides of the fingers and hand as shown in FIG. 4 and FIG. 5. In addition to holding the rod 62 stable in the patients hand, the elastic band 64 holds the metacarpophalangeal joints of the fingers in flexion. Once the desired image of the flexor retinaculum or surrounding anatomy is obtained, each adjustment can be locked to prevent additional motion in any of the adjustable directions; $R_{P-D}$, $T_{P-D}$, $R_{R-U}$, $R_{I-E}$, and $Y_{P-D}$. For example, it may be desirable to have the positioning of the imaging surface 38 of the imaging detector 12 locked in a parallel orientation with respect to the longitudinal axis $A_{FR}$ of the flexor retinaculum 22.

Figure 6:
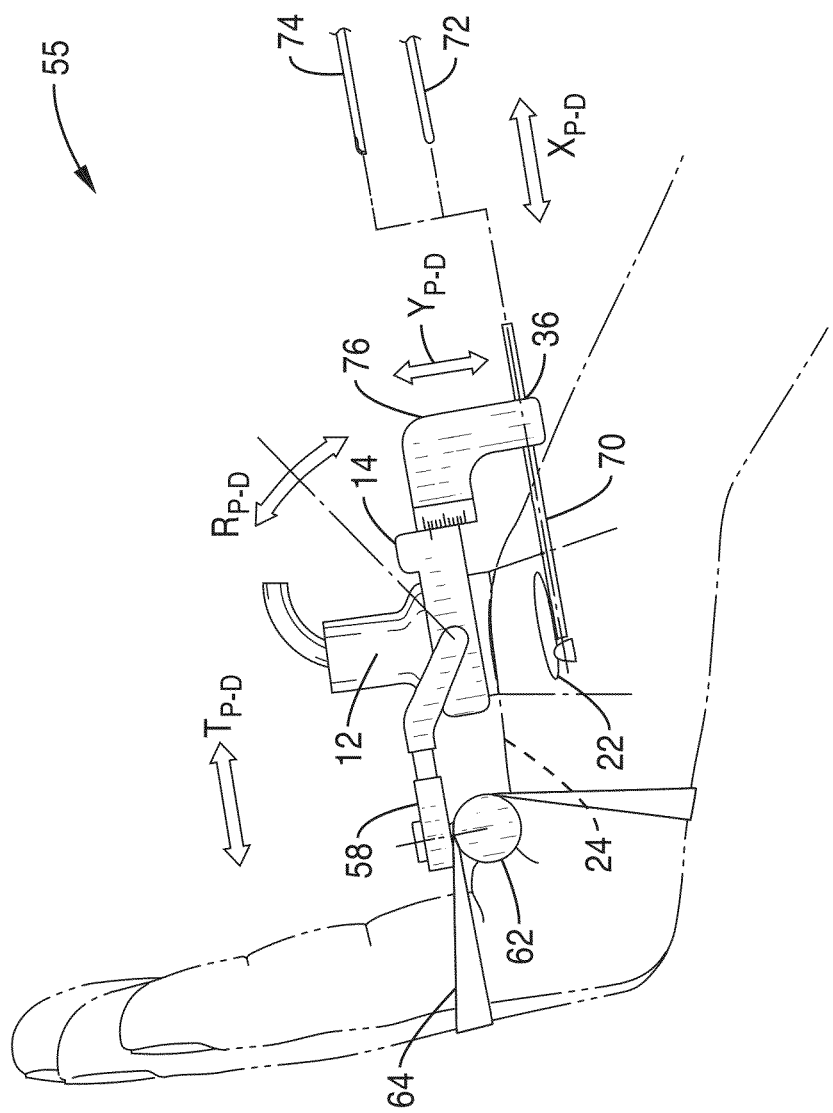
FIG. 6 is a side view of an embodiment of an injection apparatus according to the present invention similar to that shown in FIG. 4, but with the injection needle replaced with alternate devices for measurement and treatment of carpal tunnel syndrome.

FIG. 6 shows an alternative injection device 55 comprising a guide tube 70 for insertion into the carpal tunnel dorsal to the flexor retinaculum 22 (or adjacent tissue region). Similar to FIG. 3, the guide tube 70 is inserted as a conduit for alternative measurement and treatment techniques that are used either in combination with an injection of the flexor retinaculum 22 or as separate treatments. For example, diagnostic measurement of the carpal tunnel pressure may be performed using a pressure sensor 72. Either prior to or following treatment to the flexor retinaculum 22, the pressure sensor 72 is inserted through the guide tube 70 into the carpal tunnel where the pressure is measured.

Cutting probe 74 may also be delivered to the treatment site to either create a space adjacent to the flexor retinaculum or create a separation in the fibers of the flexor retinaculum for deposition of the drug. Cutting probe 74 may comprise a cutting blade, or may comprise a standard hypodermic needle with the bevel on the needle acting as a cutting blade. Either of these will enhance the ability of the flexor retinaculum to absorb the drug. In addition, cutting of the fibers of the flexor retinaculum will weaken the segment of the ligament receiving the injection. Furthermore, the cutting probe 74 may be used to perform division of the flexor retinaculum 22.

With both the attachment to the patient's hand and the adjustability provided by the apparatus shown in FIG. 6, the adjuster 76 can be used to move the guide tube 70 palmar along the palmar-dorsal direction $Y_{P-D}$ until its palmar surface contacts the dorsal surface of the flexor retinaculum 22. By squeezing the tissues between the palmar surface of the imaging detector 12 on the palm of the patient's hand 24 and the palmar surface of the guide tube 70, the guide tube 70 becomes stabilized against the deep surface of the flexor retinaculum 22.

Figure 7:
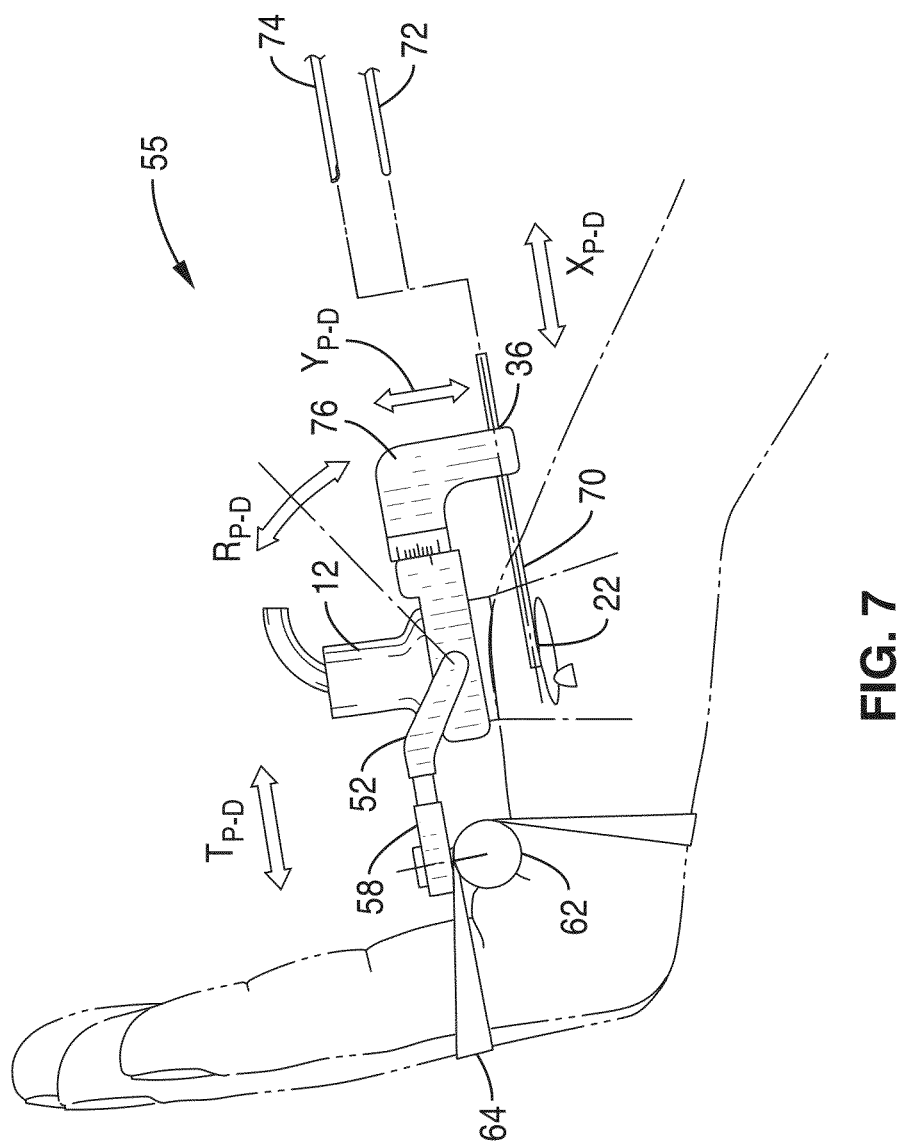
FIG. 7 is a perspective view of an embodiment of an injection apparatus according to the present invention similar to that shown in FIG. 6, but with the alternate devices for measurement and treatment of carpal tunnel syndrome shown inserted palmar to the flexor retinaculum.

FIG. 7 shows an alternative method of insertion of the guide tube 70 palmar to the surface of the flexor retinaculum 22 by moving the adjuster 76 along the palmar-dorsal direction $Y_{P-D}$ prior to insertion of the guide tube 70 into the patient's hand. A similar insertion method may be used with the injection device 49 shown in FIG. 3 using the adjuster or needle guide 16. An insertion position of the guide tube 40 or 70 palmar to the surface of the flexor retinaculum 22 could be used for insertion and treatment using the cutting probe 44 or 74 as described previously in this application.

Figure 8:
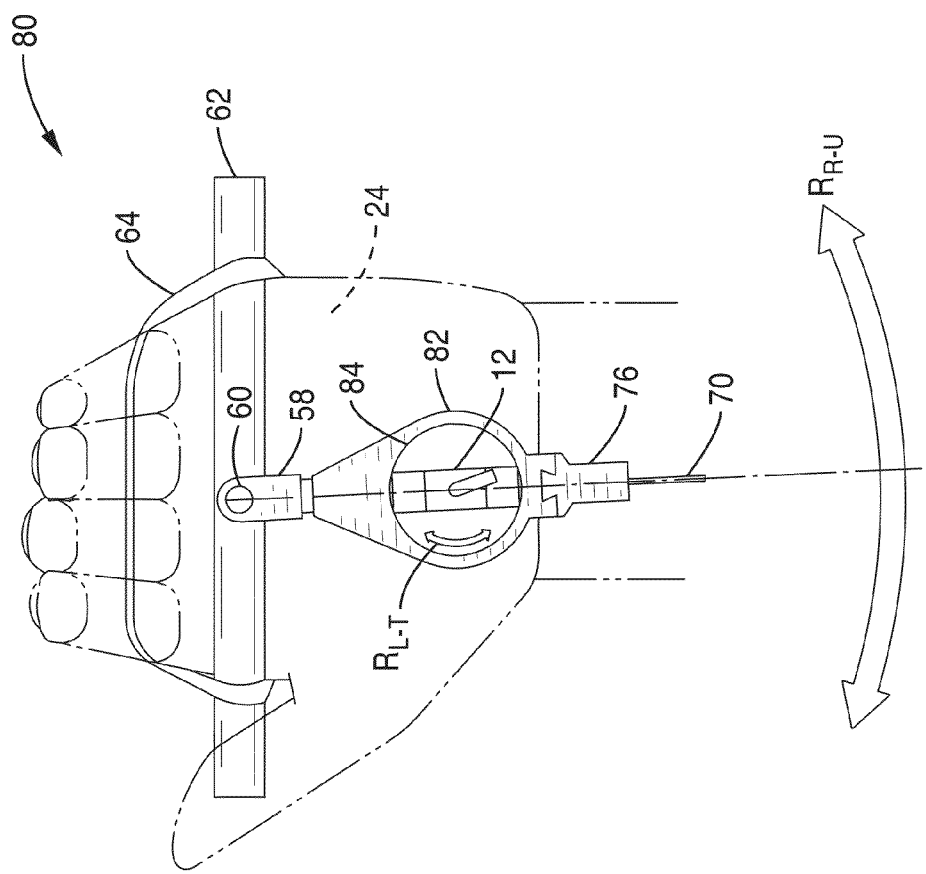
FIG. 8 is an anterior-posterior view of an embodiment of an injection apparatus according to the present invention similar to that shown in FIG. 4, but with a detector clamp that enables rotation of the imaging detector to obtain various image views.

It may be desirable for the physician to view both transverse and longitudinal images of the carpal tunnel while performing injection of the flexor retinaculum. FIG. 8 shows another embodiment of the injection device shown in FIG. 4, but with the imaging detector 12 held by a circular clamp 82. The circular clamp 82 enables rotation of the imaging detector 12 within circular opening 84 in a longitudinal-transverse direction $R_{L-T}$ about the longitudinal axis of the imaging detector $Z_D$, as shown in FIG. 2, so that images can be obtained easily in either position.

To provide stable images, the imaging detector 12 can be secured in either the longitudinal or transverse position. Alternatively, two imaging detectors either contained in a single clamp or held separately, one oriented to provide a longitudinal image and the other oriented to provide a transverse image of the patient's carpal tunnel anatomy. Using this arrangement, two images of the carpal tunnel anatomy could be displayed simultaneously on the image monitor. Another alternative embodiment is a single imaging detector with software that has the capability of providing three-dimensional images using either mechanical or electronic switching that scans using both longitudinal and transverse imaging.

Figure 9:
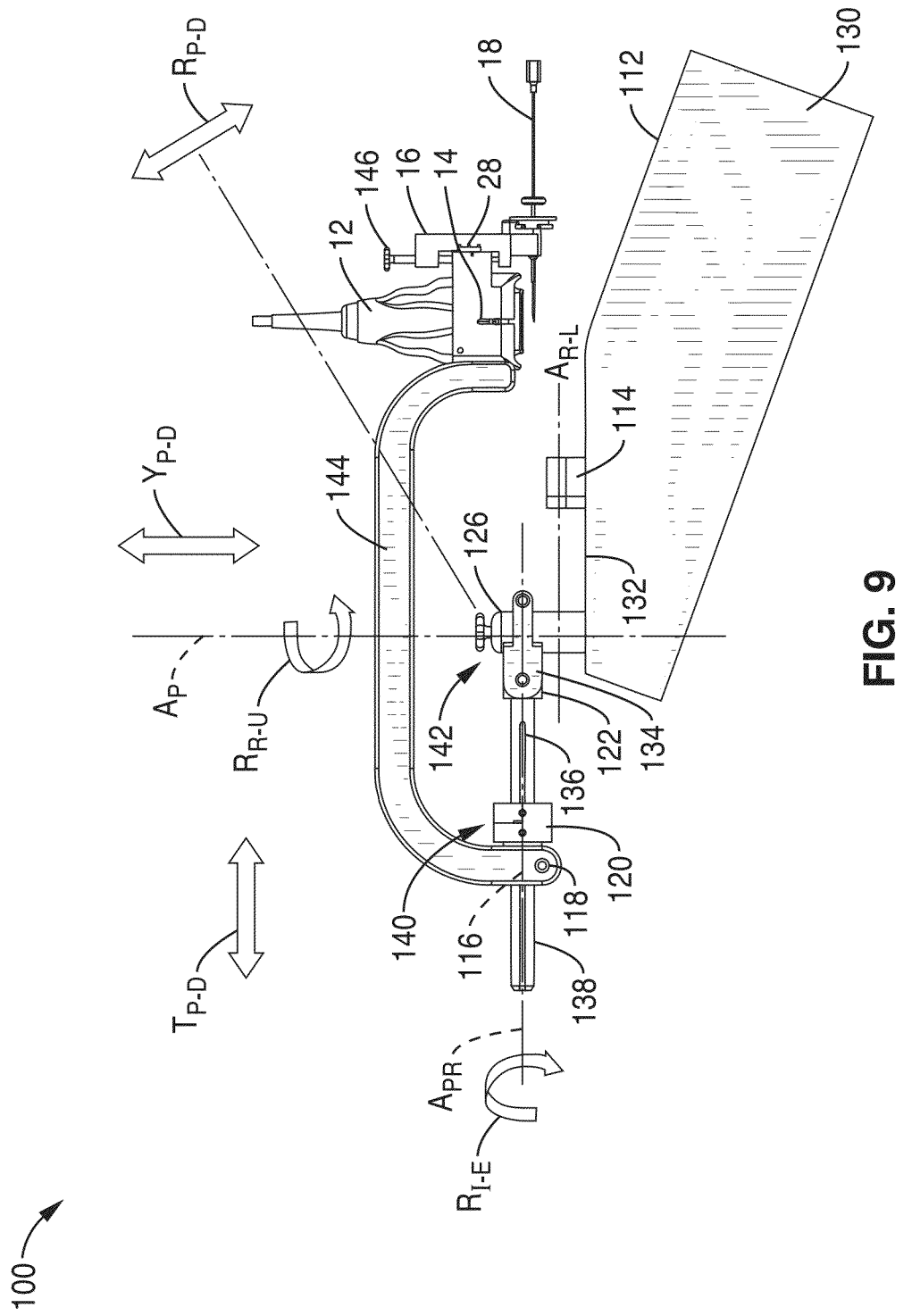
FIG. 9 is a perspective view of an embodiment of an injection apparatus according to the present invention shown with the apparatus mounted separate from the hand.
Figure 10:
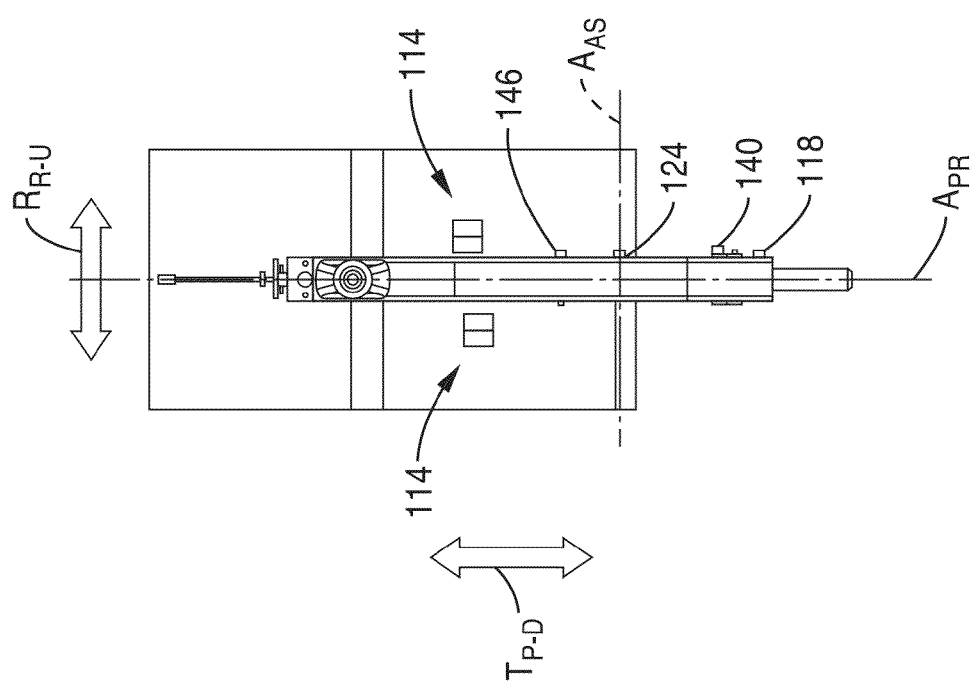
FIG. 10 is an anterior-posterior view of the injection apparatus shown in FIG. 9.

FIGS. 9 and 10 show another embodiment of an injection device 100 according to the invention for both identifying the flexor retinaculum of the carpal tunnel and injecting a drug into any part of or adjacent to the flexor retinaculum. The injection device 100 shown in FIGS. 9 and 10 is similar to that shown in FIG. 4, but instead of the alignment fixture attaching to the patient's hand, it utilizes a fixed base 130 that is used to support and hold both the patient's hand and the alignment fixture. The injection device 100 shown in FIGS. 9 and 10 also provides the same rotational and translational adjustments for alignment of the imaging detector 12 and needle guide 16 as those provided by the injection device 50 shown in FIG. 4; thereby maintaining both support and alignment of the imaging detector 12 and needle guide 16 when the physician releases their hold of the imaging detector 12.

The top surface of the base 130, where the patient's forearm and hand are supported, consists of a flat surface 112 where the patient's forearm rests and an angled surface 132 that supports the patient's hand. Positioning the back or dorsal surface 25 (see FIG. 4) of the patient's hand (which has less soft tissue than the palmar surface 24) on the angled surface 132, the hand may be reliably positioned on the second surface in a stable manner that allows little, if any motion of the hand with respect to the second surface. The angle between the two surfaces is aligned with the patient's wrist to position the wrist in an appropriate degree of extension to accommodate entry of the injection needle 18. With the patient's hand resting on the angled surface 132, both their index and little fingers may be constrained by straps 114 that prevent these two fingers from flexing while allowing the other two fingers and thumb free to flex. The clamp 14 that secures to the imaging detector 12 is attached to an arm 144 that has a hole 116 in its distal end. A rotational adjustment screw 118 is used to secure the arm 144 to a positioning rod 138 that inserts through the hole 116. Loosening of the rotational adjust screw 118 enables rotation of the arm 144 about the longitudinal axis $A_{PR}$ of the positioning rod 138 to provide tilting of both the imaging detector 12 and needle guide 16 in an internal-external direction $R_{I-E}$.

Loosening of the translational adjustment screw 140 on the slide block 120 permits translation of the arm 144 along a slot 136 in the positioning rod 138, allowing translation in a proximal-distal direction $T_{P-D}$. The proximal end of the positioning rod 138 inserts into a pivot block 122 that attaches to a clevis clamp 134 using a tilt adjustment screw 124. Loosening of the tilt adjustment screw 124 allows rotation of the pivot block 122 about the longitudinal axis of the tilt adjustment screw $A_{AS}$, permitting the arm 144, imaging detector 12, and needle guide 16 to rotate in a palmar-dorsal direction $R_{P-D}$.

Loosening of the clevis clamp screw 146 allows rotation of the clevis clamp 134 about the longitudinal axis $A_P$ of the post 126, permitting the arm 144, imaging detector 12, and needle guide 16 to rotate in a radial-ulnar direction $R_{R-U}$. The longitudinal axis $A_P$ of the post 126 is both perpendicular to and intersects with a longitudinal axis $A_{RL}$ that forms the contact line between the patient's ring and long fingers. An adjustment knob 142 is used to translate the post 126 in a palmar-dorsal direction $Y_{P-D}$, providing translation of both the imaging detector 12 and needle guide 16 along the same direction $Y_{P-D}$.

In the embodiments shown above, the drug 34 is contained in a syringe 20 or the like. In an alternative embodiment, the drug 34 can be contained in a pre-packaged cartridge (not shown) that is pre-filled with the appropriate dosage of drug 34. This pre-filled cartridge can then be inserted into any suitable standard manual drug delivery device with a needle. A pre-packaged dosage of the drug 34 may also include particles to enhance the image of the drug 34. Other alternative embodiments include any suitable drug delivery device that uses a pressure mechanism to dispense the drug.

Prior to insertion of any of the previously described injection needles, pressure sensors, guide tubes, or cutting probes, local anesthesia may be administered by injecting it into the patient's wrist or hand. Injection of local anesthesia may be performed using either the injection needles described or a separate standard injection needle. Local anesthesia may be injected either alone, separately, or combined with the drug 34.

The flexor retinaculum inherently has a physiologic tension that exists primarily in a radial-to-ulnar direction as a result of its anatomy. The exact mechanics related to this tensile stress aren't completely understood. However, attachments of the thenar and hypothenar muscles to the collagen fibers of the flexor retinaculum contribute to this tensile stress. This tensile stress, which determines the strength of the flexor retinaculum, exists in order to maintain the structural integrity of the carpal tunnel during both static and dynamic hand activities. Whether the hand is at rest or active, the tension in the flexor retinaculum is sufficient to balance the forces acting on it; one of which is the variable pressure that exists within the carpal tunnel. It is this pressure that exists within the carpal tunnel that can be used to increase the stress in the collagen fibers of the flexor retinaculum once they have been weakened by injection of a drug.

With the hand at rest, a pressure exists within the carpal tunnel, and that pressure is greater in subjects with CTS than those without. During both forceful grip and pinch, pressure within the carpal tunnel increases substantially, thereby causing an increase in tensile stress in the flexor retinaculum.

In twenty patients with CTS, pressure was measured within the carpal tunnel, adjacent the flexor retinaculum, as patients actively used their hands. As patients gripped a grip dynamometer using 25% maximum grip, 50% maximum grip, and maximum grip, the pressures adjacent the flexor retinaculum increased significantly. The mean peak pressure during maximum grip was 1151 mm Hg, with pressures as great as 2500 mm Hg recorded. As patients pinched a pinch dynamometer using maximum pinch, the pressures adjacent the flexor retinaculum reached a mean peak of 621 mm Hg, with pressures as great as 1133 mm Hg recorded. Test results showed that pressures in the carpal tunnel were up to eight times greater than those previously recorded.

To produce the required tensile stress in the weakened collagen fibers of the flexor retinaculum, the physician can prescribe an active hand use protocol for the patient.

During a period of time after injection of the drug, while the drug remains effective, the inherent stress in the flexor retinaculum may be sufficient, with the weakened collagen fibers, to cause either rupture of the collagen fibers or an increase in their length resulting from their growth over time. However, if the inherent stress in the flexor retinaculum is insufficient to obtain the desired improvement in patient symptoms, the physician should prescribe for the patient to perform forceful and repetitive gripping or pinching exercises. These exercises may be performed either with or without the aid of either a grip device that fits in the palm of the patient's hand or a pinch device that fits between the thumb and one or more fingers. Grip or pinch exercises that achieve pressures comparable to those recorded during the study would provide the increase in tensile stress necessary to cause the collagen fibers composing the flexor retinaculum to either abruptly fail and/or increase in anatomic length. To ensure that the patient performs the prescribed grip or pinch exercises, any standard commercially available grip or pinch dynamometers can be used that have the capability to provide either visual or auditory feedback to the patient of both the magnitude of grip or pinch force and the number of grips or pinches that have been performed. Grip or pinch exercises are continued daily until the drug is no longer effective at weakening the structural integrity of the collagen. Even after the drug affect has expired, hand exercises should be continued to maintain the increased length and decreased strength of the flexor retinaculum.

Figure 11:
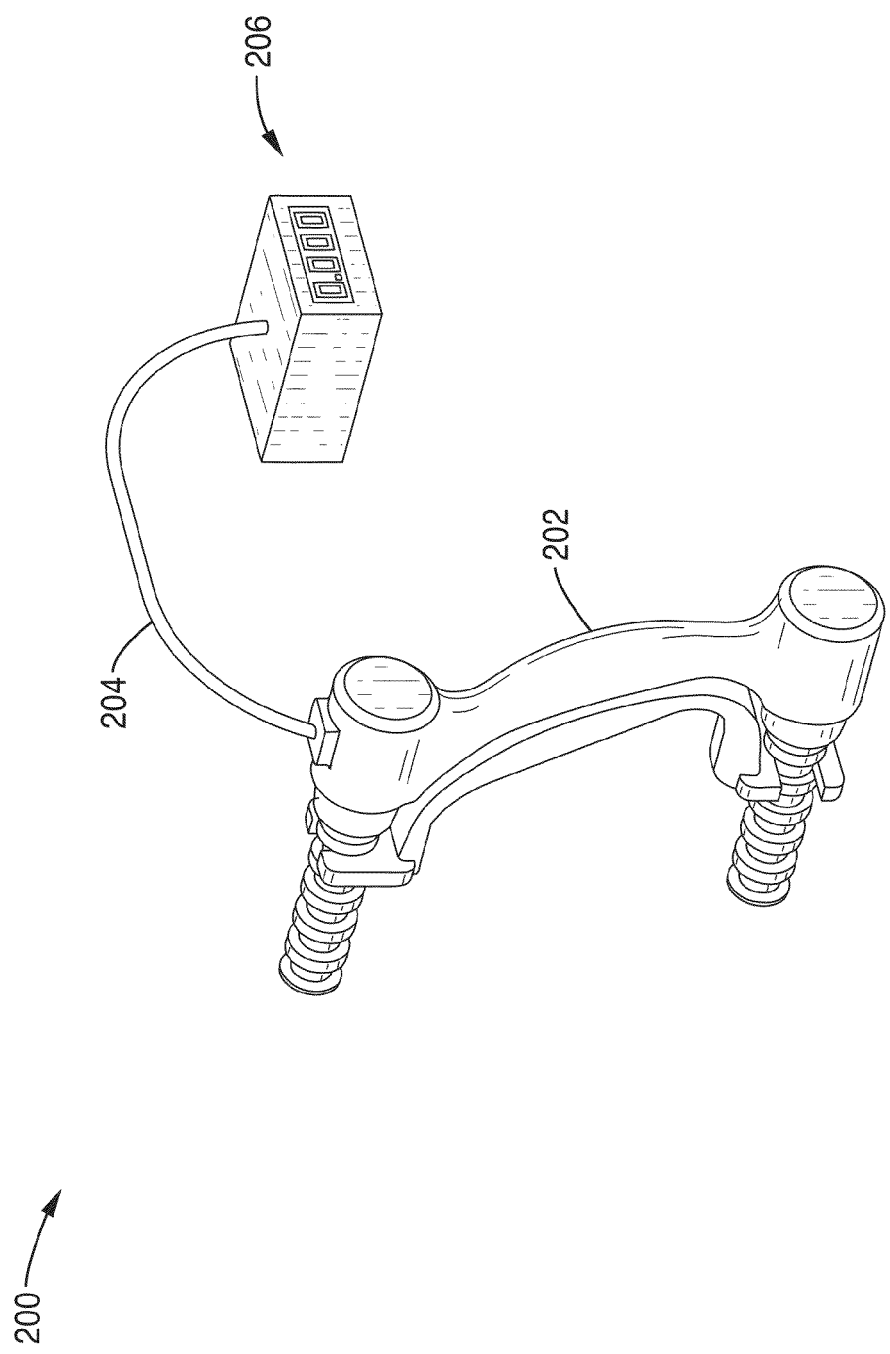
FIG. 11 is a perspective view of a standard grip dynamometer with data acquisition and display module.
Figure 12:
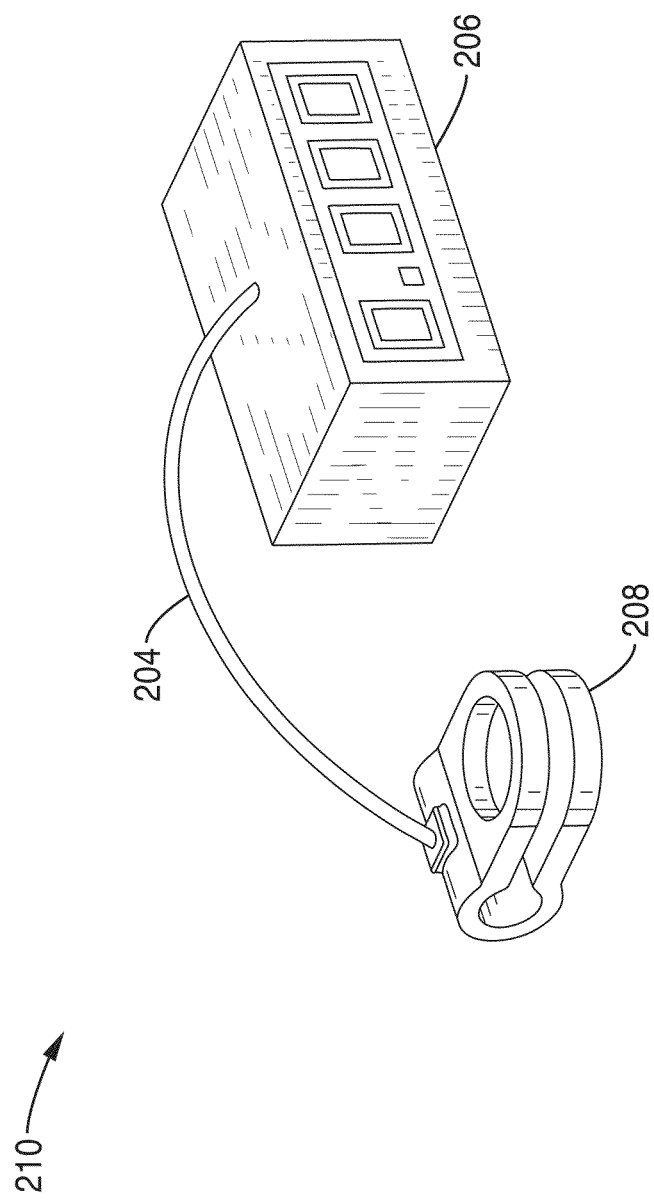
FIG. 12 is a perspective view of a standard pinch dynamometer with data acquisition and display module.

FIG. 11 illustrates system 200 comprising a standard grip dynamometer 202. FIG. 12 shows system 210 having pinch dynamometer 208. Standard commercially available dynamometers are manufactured by JAMAR Technologies, JTECH Medical, and others. Each dynamometer can be attached through cabling 204 to a data acquisition and display module 206. Display module 206 aids the patient by displaying their force magnitude and number of grip or pinch cycles while performing the prescribed grip or pinch exercises. In addition, the patient's force data is stored in the data acquisition and display module 206 and provides the physician with a record of the force magnitudes achieved, the amount of time the patient spent at each force level, and number of cycles of each.

Alternatively, an exercise device may apply force to the palm of the patient's hand that increases the pressure within the carpal tunnel. However, using this method, the stress produced in the flexor retinaculum may be less than that produced by a patient initiated force. In the experiments of the present invention, the pressure produced in the carpal tunnel, adjacent the flexor retinaculum, when an external grip dynamometer was used to apply the same force to the palm of the patient's hand, was one-half of what the pressure was when the patient generated the force themselves using the same grip dynamometer. It is during active grip activities with advanced degrees of finger flexion that the lumbrical muscles of the hand migrate proximally into the carpal tunnel, providing the dilating force necessary to cause the maximum increase in tensile stress in the flexor retinaculum.

If complete relief of the symptoms of CTS is not achieved with either a single dose injection or multiple doses during a single day, additional injections using the methods described previously in this application can be performed over time, followed by a prescribed hand exercise routine. Subsequent injections may be based on either the patient's symptoms or the active life of the drug.

Alternatively, additional injections may be facilitated by inserting a standard commercially available catheter (not shown), with or without multiple perforations, via the guide tube 40 shown in FIG. 3 or guide tube 70 shown in FIG. 7. The gauge of guide tube 70 may be modified accordingly. After insertion, the catheter may be left in place to provide intermittent injections of a drug either into or adjacent the flexor retinaculum.

The methods and apparatus described in FIGS. 1-12 above for the treatment of carpal tunnel syndrome may also be used for the treatment of other diseases involving a ligament that constrains either a tendon or nerve, including, but not limited to, tarsal tunnel syndrome of the foot, trigger finger, trigger thumb, tendonitis of the long head of the biceps tendon in its groove in the proximal humerus at the shoulder joint, cubital tunnel syndrome, and DeQuervains tendonitis at the wrist. Injection of a drug either into or adjacent the ligaments that form the pulleys for these anatomical locations would prove effective for treating these diseases.

As the mechanical properties of the flexor retinaculum change over time following the injection, relief of the patient's symptoms may be used to monitor the effectiveness of the injection. Other alternative methods may be used to monitor the effectiveness of the injection including nerve conduction tests and pressure measurements within the carpal tunnel. Another alternative method is to monitor the physical behavior of the flexor retinaculum using ultrasound imaging. A series of ultrasound images following treatment of the flexor retinaculum can be used to monitor the response of the flexor retinaculum to the drug and exercise program. Another alternative to monitor the effectiveness of the injection includes blood and/or urine samples to assay for the breakdown products of collagen in general and collagen that makes up the flexor retinaculum in particular.

The methods and apparatus of the present invention provide for injection of a drug either into any part of or adjacent to the flexor retinaculum followed by increasing the tensile force to the weakened collagen fibers of the flexor retinaculum to relieve the symptoms of CTS. This provides several advantages over prior techniques for the treatment of CTS, including (a) prevention of excessive palmar displacement of the digital flexor tendons and/or median nerve created by the traditional division of the flexor retinaculum; (b) avoiding entrapment of the median nerve and/or flexor tendons in a more nearly subcutaneous palmar position in which these structures are relatively or absolutely entrapped in scar tissue that occurs as a result of the healing process for the surgically divided flexor retinaculum; (c) maintenance of relative stability of the entire flexor retinaculum as a unit, e.g., the cut edges of the completely divided flexor retinaculum can evert (turn outward or subcutaneously) as a result of the spread of the carpal tunnel, as well as the pull of the thenar and hypothenar muscle groups, particularly the thenar muscles on the radial side of the divided flexor retinaculum; (d) preservation of a gliding synovial surface on the deep side of the flexor retinaculum for the digital flexor tendons and median nerve; (e) potential decreased morbidity from greater stability of the origin of the muscles that arise from the flexor retinaculum, particularly the thenar muscles responsible for thumb opposition, pinch and grasp; (f) decrease in the amount of time necessary to return to activities of daily living and work as a result of less trauma caused to the flexor retinaculum; (g) reduced costs of treating CTS, including performing the ligament injection as an office procedure rather than an operating room procedure; (h) the inherent safety of an injection needle that is guided using ultrasound imaging compared with a cutting blade used for open or endoscopic carpal tunnel release; (i) avoiding shear stress on the median nerve where the ligament/fascia division abruptly stops, typically at the proximal end of the incised ligament/fascia; and (j) the decreased potential for a hematoma in the carpal tunnel that may, as the hematoma evolves, entrap the median nerve in scar tissue.

EXAMPLE

Tests were performed to better understand the dynamics of intracarpal tunnel pressure from proximal-to-distal in patients with CTS during quantified active use of the hand both before and after division of the transverse carpal ligament.

The test included 20 patients (21 hands: 10 left, 11 right), 11 female and 9 male (mean age: 55 years; range: 33-81 years), diagnosed with idiopathic CTS. In each patient, the diagnosis of idiopathic CTS was based on clinical signs and symptoms and confirmed by preoperative electrophysiological studies. The mean time from diagnosis to surgery was 2 years and 11 months (range: 2.5 months-15 yr. 3 months.). In addition, at least one steroid injection was administered to twenty of the affected hands and was used to confirm the diagnosis based on relief of symptoms. Patients were excluded from the study if there was any history of peripheral neuropathy, diabetes, thyroid disease, anatomic abnormalities of the wrist or hand, inflammatory joint disease, previous traumatic nerve injury, previous wrist surgery, vasospastic disorders or sympathetic dystrophies, psychiatric disorders, chronic renal disease, or previous carpal tunnel release. The hospital institutional review board approved the study protocol and both informed consent and HIPAA authorization were obtained from each patient.

Figure 13:
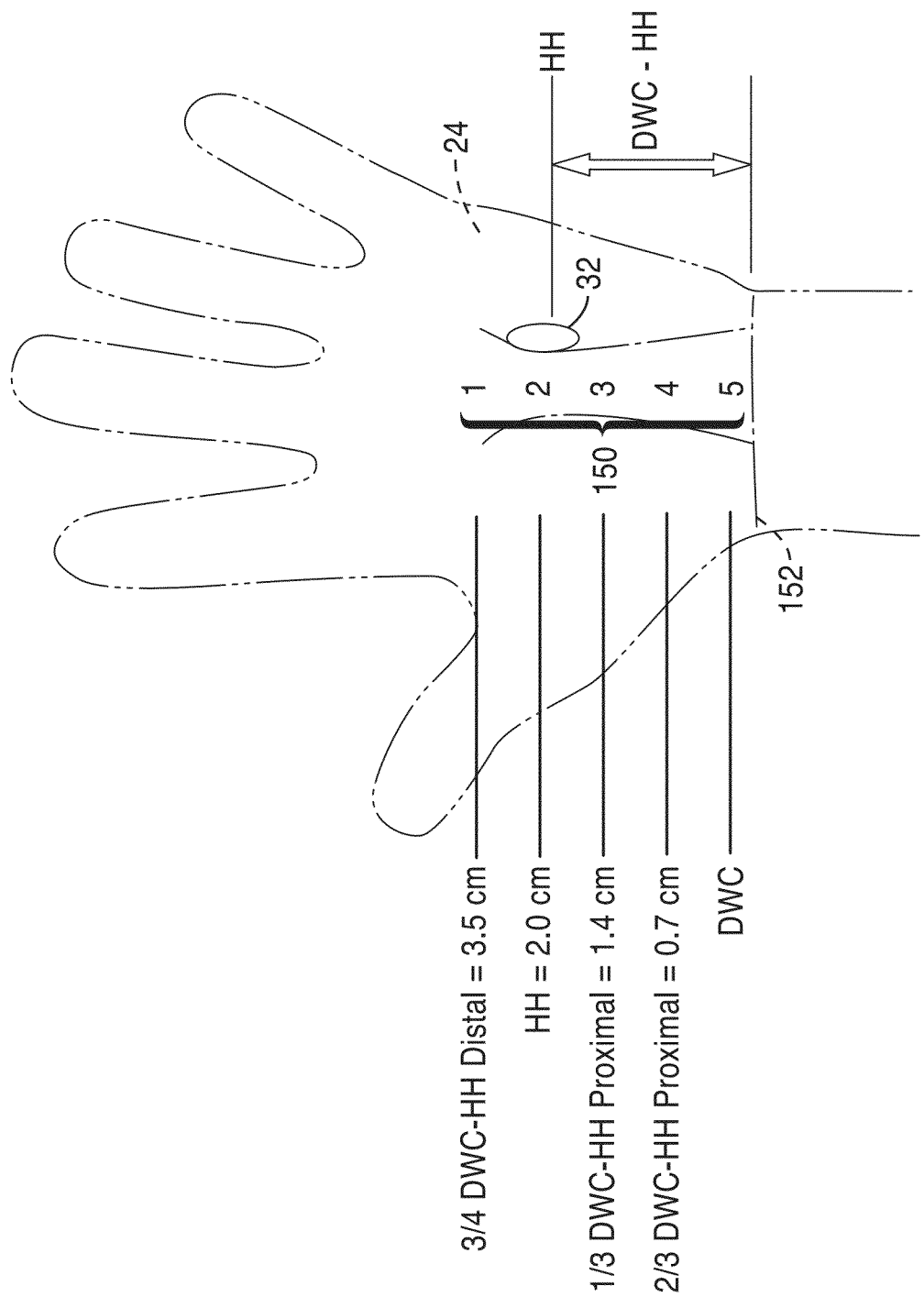
FIG. 13 illustrates a hand with indicated measurement locations chosen and standardized based on a DWC-HH measurement.

Referring to FIG. 13, prior to surgery for CTS, an anterior-posterior radiographic view was obtained on each patient to identify the proximal-to-distal distance between the distal wrist crease (DWC) 152 and the center of the Hook of the Hamate (HH) 32. This dimension, DWC-HH (mean: 2.0 cm; range: 1.6-2.5 cm), was used for two purposes. The first purpose was to establish a visual landmark on the skin, at the time of surgery, identifying HH relative to the easily identifiable DWC. The second purpose was to standardize the proximal-to-distal locations where pressure measurements were recorded based on the individual anatomy of each patient.

As shown in FIG. 13, five measurement locations 150 were chosen and standardized based on the DWC-HH measurement.

Also prior to surgery, maximum grip and pinch forces were determined for each patient. Maximum grip force was measured using a handheld grip dynamometer 202 (see FIG. 15) (Griptrack; Jtech Medical, Salt Lake City, Utah) calibrated for 0 to 456 N. Patients performed three maximum grip trials with the grip spacing set to the smallest. With this grip spacing, the mean distance between the tip of the ring finger and the palm of the hand was 30 mm (range: 22-48 mm). From the grip trials, a mean maximum grip force was computed for each patient and 75% of that value was used as the patient's maximum grip force (MGF). Maximum pinch force was measured using a pinch dynamometer 204 (see FIG. 16) (Pinchtrack; Jtech Medical, Salt Lake City, Utah) calibrated for 0 to 222N. Patients performed three maximum pinch trials each using both pulp and key pinches. Mean maximum pinch forces were computed for both pulp and key pinches on each patient and 75% of these values were used as the patient's maximum pulp pinch force (MPF) and maximum key pinch force (MKF). During both grip and pinch force measurements, patient's wrists were maintained in a neutral position. 75% of the patient's maximum grip and pinch forces were chosen as MGF, MPF, and MKF to ensure that each patient could achieve these forces during surgery. Once MGF, MPF, and MKF were determined, each patient practiced both achieving and holding the target grip and pinch force levels that they would perform during their surgery, using visual feedback of the force levels.

On the day of surgery, each patient was prepared for an endoscopic carpal tunnel release. Using the DWC-HH landmark obtained from the preoperative radiographic view, each patient's hand was marked with the location of HH 32. Next, a brachial tourniquet was applied and, under local anesthesia, an entry wound through the fascia was created approximately 1 cm proximal to DWC between the flexor carpi radialis and flexor carpi ulnaris tendons. This wound at the wrist provided access deep to the fascia for insertion of a pressure transducer PT (see FIG. 14). Two types of entry wounds were used, either an incision or a percutaneous. The incision entry, used on 13 hands, was the endoscopic portal used with the MicroAire Carpal Tunnel Release System (MicroAire, Charlottesville, Va.) that was described previously. The percutaneous entry, used on 8 hands, was created using a 13-gauge hypodermic needle (BD Medical Systems, Franklin Lakes, N.J.) with a custom-made obturator. In both entry methods, once access deep to the fascia was established, a 2.5 mm probe was used to create a path from proximal to distal down the palmar-ulnar aspect of the carpal tunnel for insertion of the pressure transducer.

Figure 14:
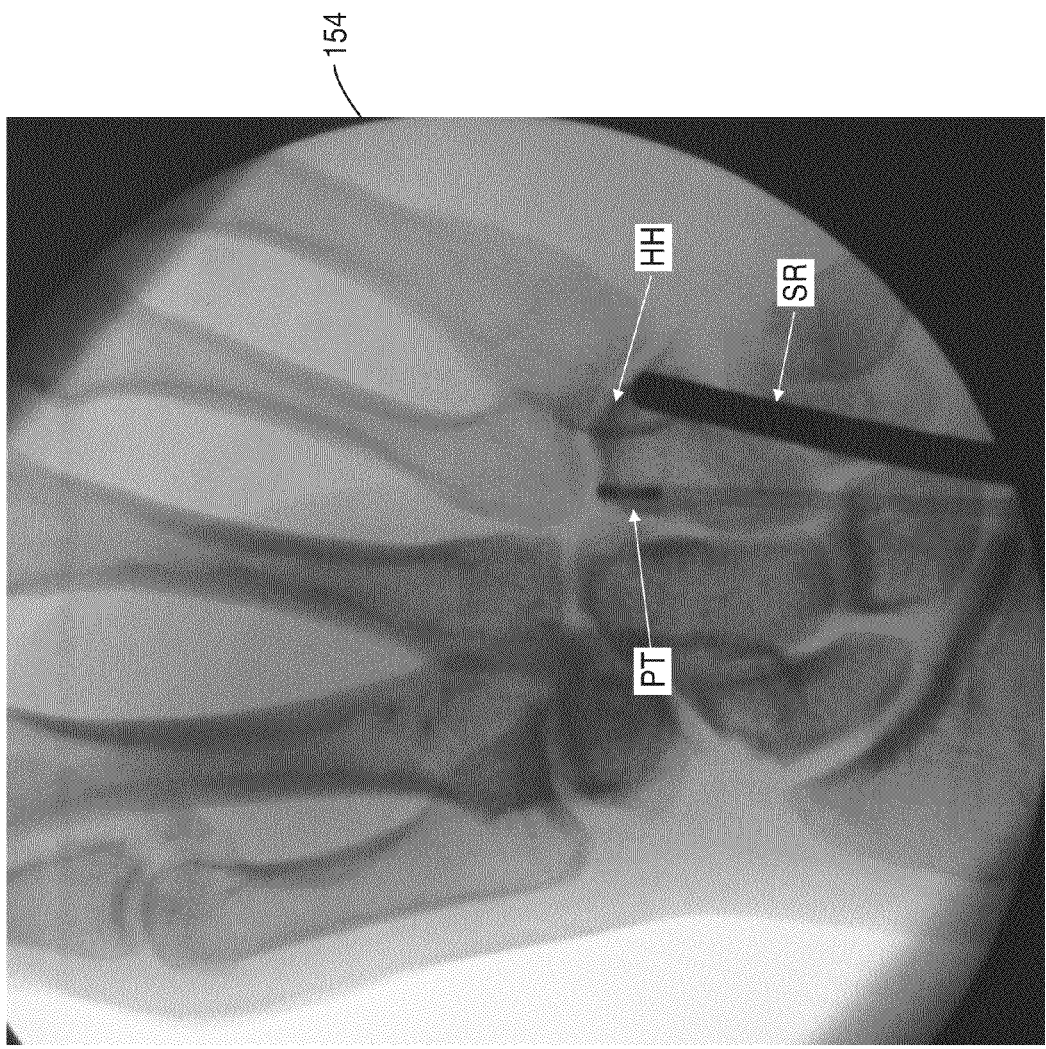
FIG. 14 illustrates placement of a pressure sensor confirmed using fluoroscopy.
Figure 15:
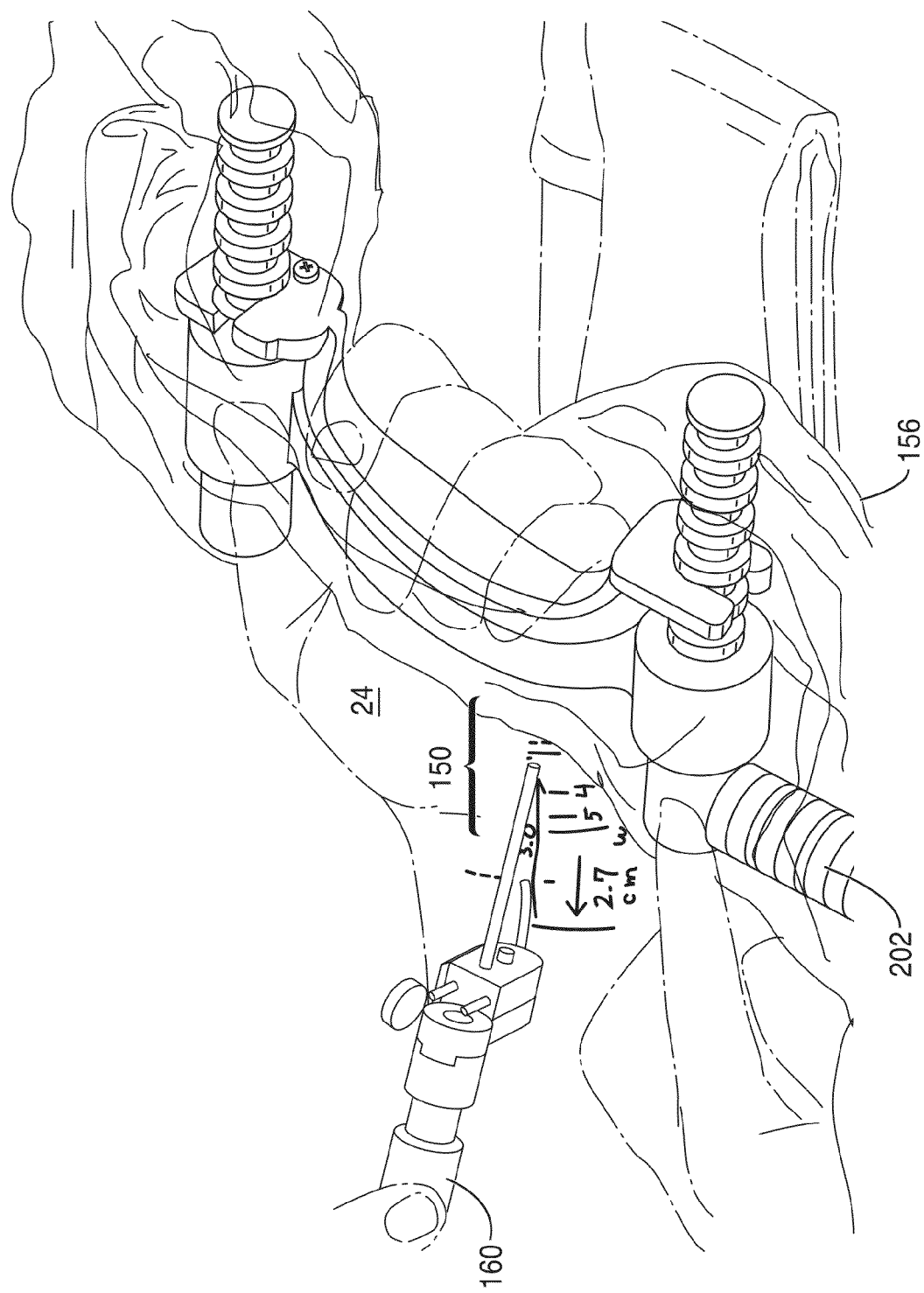
FIG. 15 illustrates testing for measurements made on a patient's hand for maximum grip force (MGF).
Figure 16:
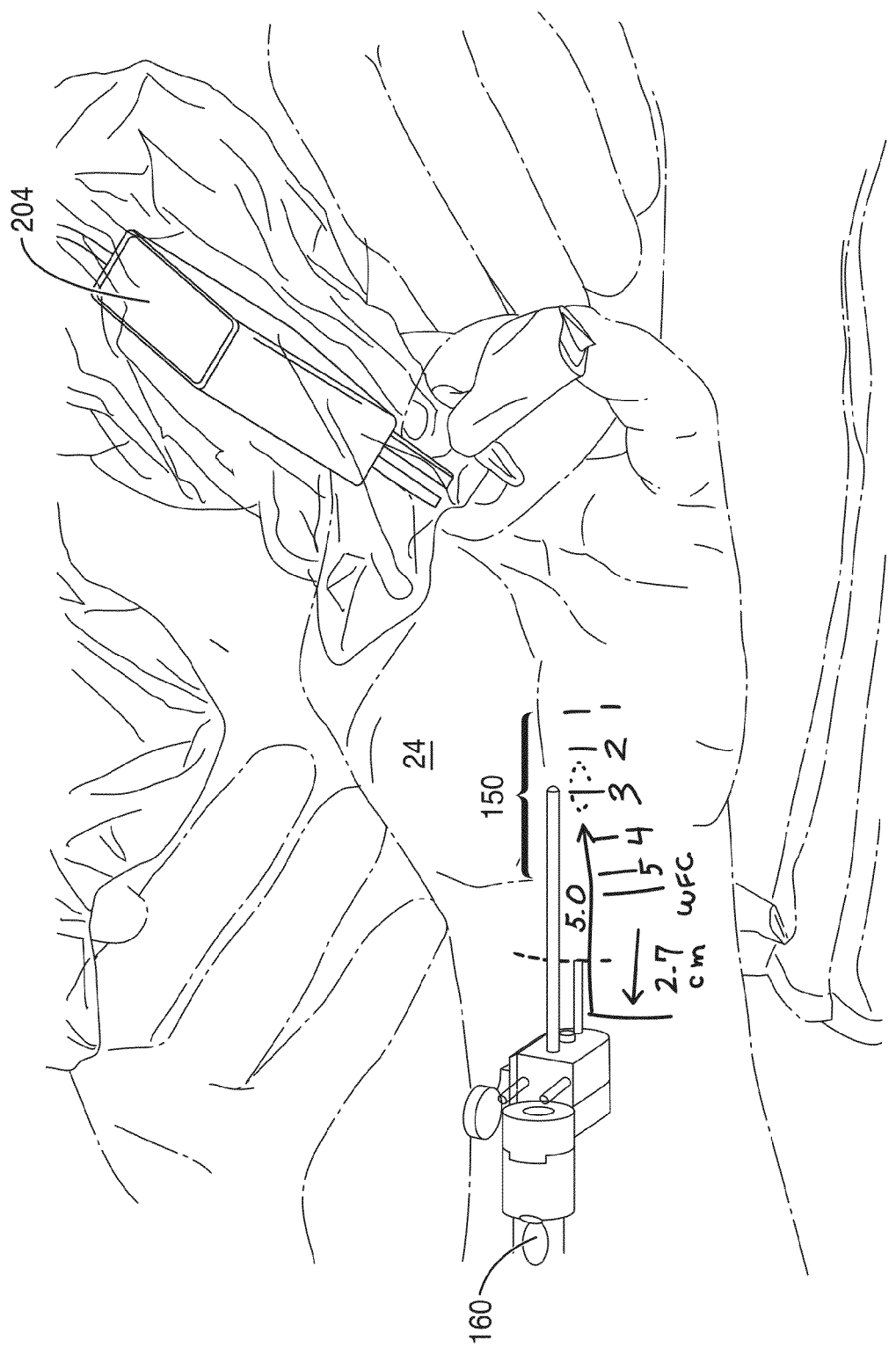
FIG. 16 illustrates testing for measurements made on a patient's hand for maximum pulp pinch force (MPF).
Figure 17:
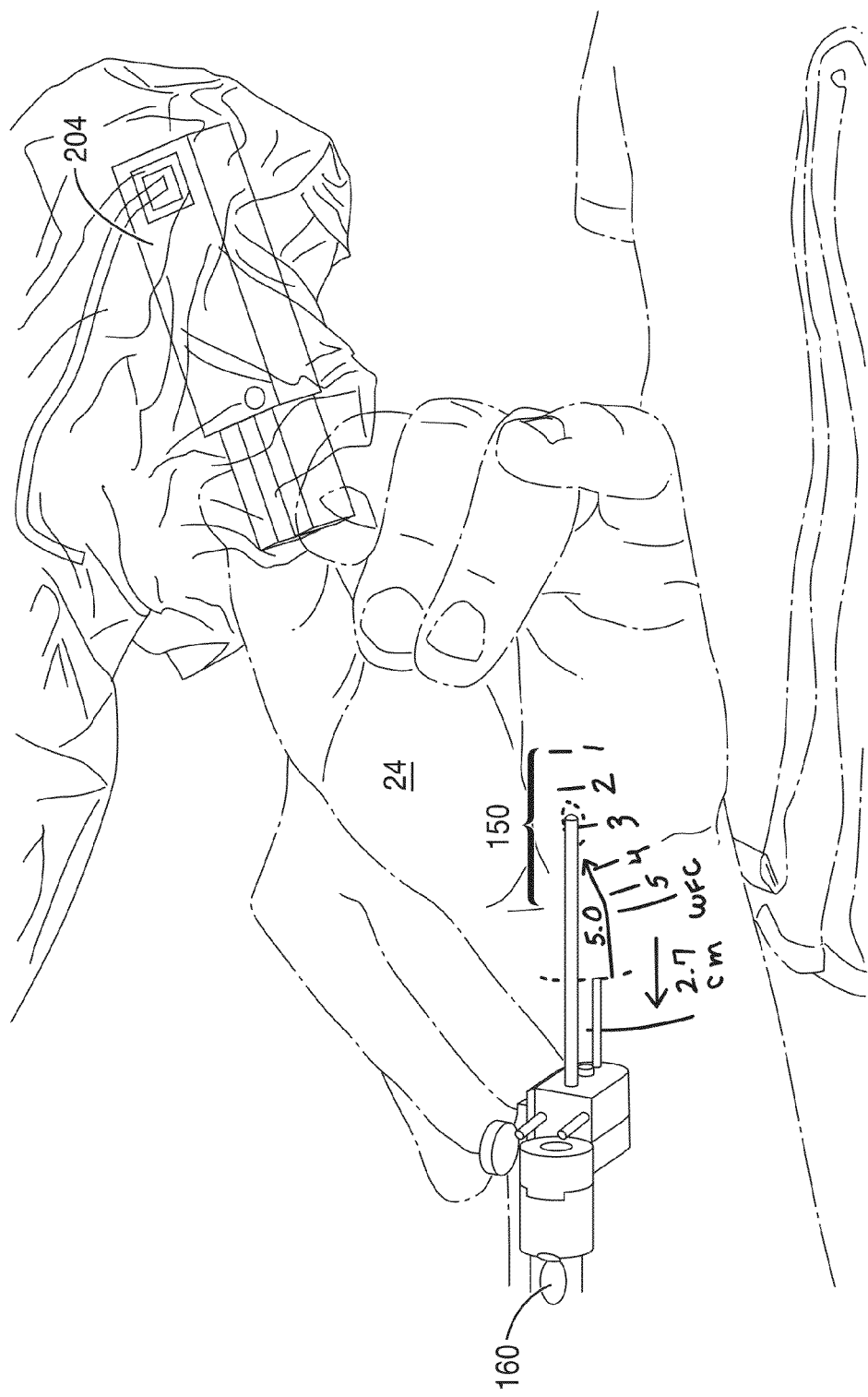
FIG. 17 illustrates testing for measurements made on a patient's hand for maximum key pinch force (MKF).

Intracarpal tunnel pressures were measured using a MIKRO-TIP pressure transducer PT (SPC-3505; Millar Instruments, Houston, Tex.) containing a miniature semiconductor gauge pressure sensor in a 5F catheter (cross-sectional area=2.2 $mm^2$) calibrated for a measurement range of −50 to 3000 mm Hg. The pressure transducer PT was inserted through the entry wound, along the path created down the palmar-ulnar aspect of the carpal tunnel, and aligned adjacent both HH and the dorsal surface of the transverse carpal ligament with the sensor oriented dorsal. The tourniquet was released (mean tourniquet time: 7 minutes; range: 4.5-11 minutes) and reperfusion of the tissues was allowed (mean reperfusion time: 8.5 minutes; range: 5-17 minutes) before pressure measurement began. During reperfusion, correct placement of the pressure sensor PT at HH was confirmed using fluoroscopy (see fluoroscopic image 154 in FIG. 14). In addition, a custom-made clamp 160, used to both hold and position the pressure transducer PT, provided a visual reference of its position within the carpal tunnel using an external solid rod SR (FIG. 14). This enabled marking the standardized pressure measurement locations 150 on the palmar skin 24 (FIG. 15).

With the patient's upper extremity resting on an arm table, elbow extended, forearm supinated, and wrist in a neutral position, pressure measurements were obtained at each of the five standardized locations 150 within the carpal tunnel in the following order: ¾ DWC-HH distal to HH, HH, ⅓ DWC-HH proximal to HH, ⅔ DWC-HH proximal to HH, DWC, and a repeat measurement at HH. At each location, with either minimal or no sedation, the patient performed each of the following hand activities: fingers fully extended, fingers fully flexed without grip force, 25% MGF, 50% MGF, MGF (FIG. 15), MPF (FIG. 16), MKF (FIG. 17), and fingers fully extended while an external force was applied by the physician to the patient's hand using 25% MGF, 50% MGF, and MGF.

Intracarpal tunnel pressure was recorded simultaneously with grip force, pinch force, and external force using signal conditioning hardware (Validyne Engineering, Northridge, Calif.) with a portable data acquisition system (Mycorder; Datastick Systems, Santa Clara, Calif.). Both grip and pinch forces were measured using the same dynamometers 202 and 204 that patients used prior to surgery, but they were enclosed in sterile bags. The external force was applied by the physician pressing the same grip dynamometer 202 against the palm 24 of the patient's hand in the same location where the patient held it. As the patient received instructions, visual feedback of both grip and pinch force was provided to the patient, enabling each patient to both achieve and maintain the target force levels.

Once all pressure measurements were obtained, the pressure transducer PT was removed, the tourniquet was reapplied, and endoscopic carpal tunnel release surgery was performed. After complete division of the transverse carpal ligament, the tourniquet was released, reperfusion was allowed for five minutes, and the pressure transducer PT was reinserted into the carpal tunnel. Pressure measurements were obtained with the transducer positioned at a single location, HH, during the same hand activities, with the exceptions of MGF and application of an external force.

All pressure measurements were expressed as the mean±one Standard Error (SE). Using a log transformation on the data, a repeated measures analysis of variance was used to determine the affect of hand activity, intracarpal measurement location, and surgical division of the ligament on intracarpal tunnel pressure. A Tukey-Kramer analysis with a significance level of $p<0.05$ was used to adjust for multiple comparisons.

Standardized pressure measurement locations resulted in mean distances distally from DWC of 0.7 cm (range: 0.6-1.3 cm), 1.4 cm (range: 1.1-2.0 cm), 2.0 cm (range: 1.6-2.3 cm), and 3.5 cm (range: 2.9-4.1 cm) (FIG. 13).

Figure 18:
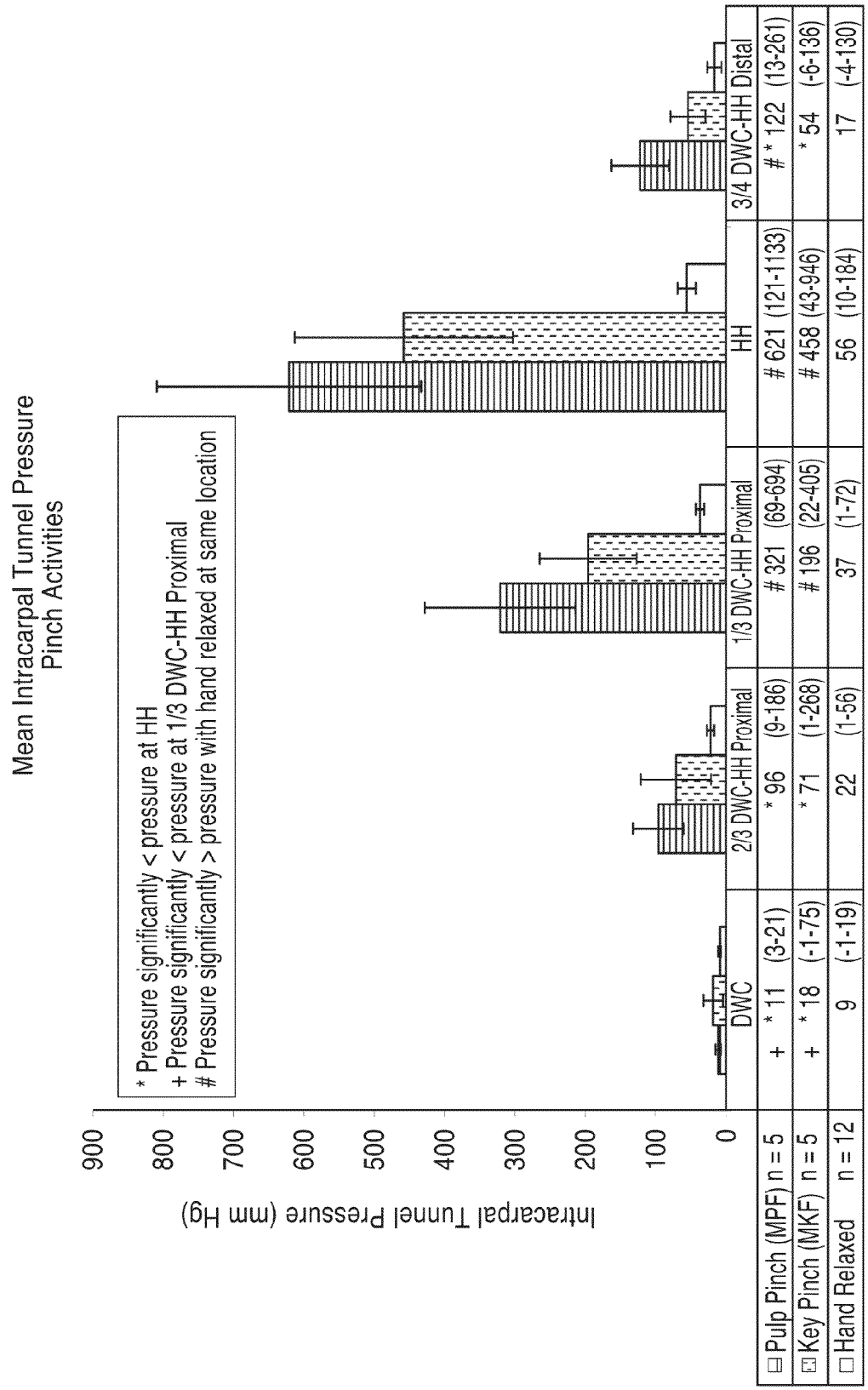
FIG. 18 is a graph comparing mean intracarpal tunnel pressures measured at the five standardized proximal-to-distal locations 150 for hand relaxed and pinch activities.
Figure 19:
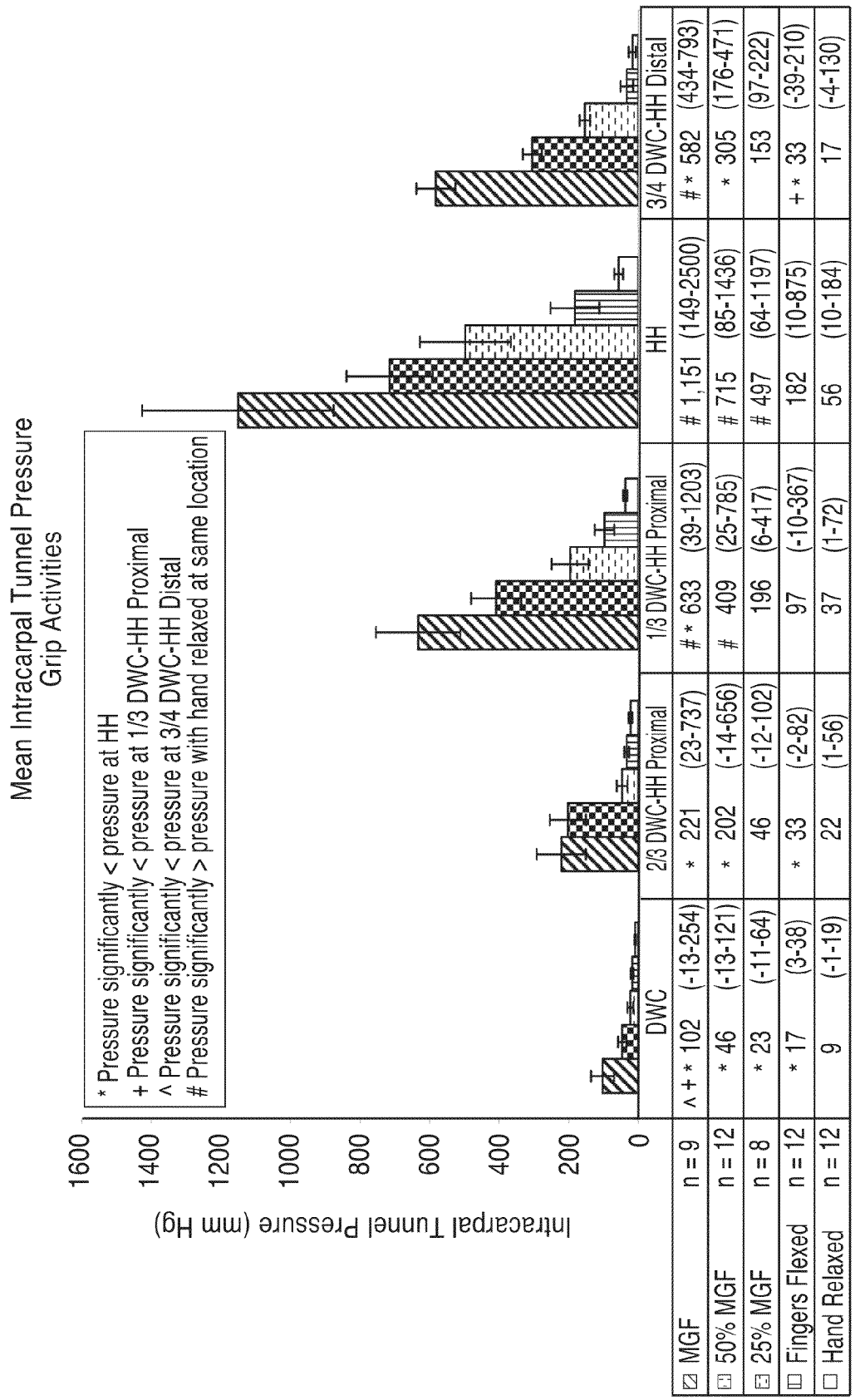
FIG. 19 is a graph comparing mean intracarpal tunnel pressures during hand relaxed, fingers flexed, and grip activities at the five standardized proximal-to-distal locations.
Figure 20:
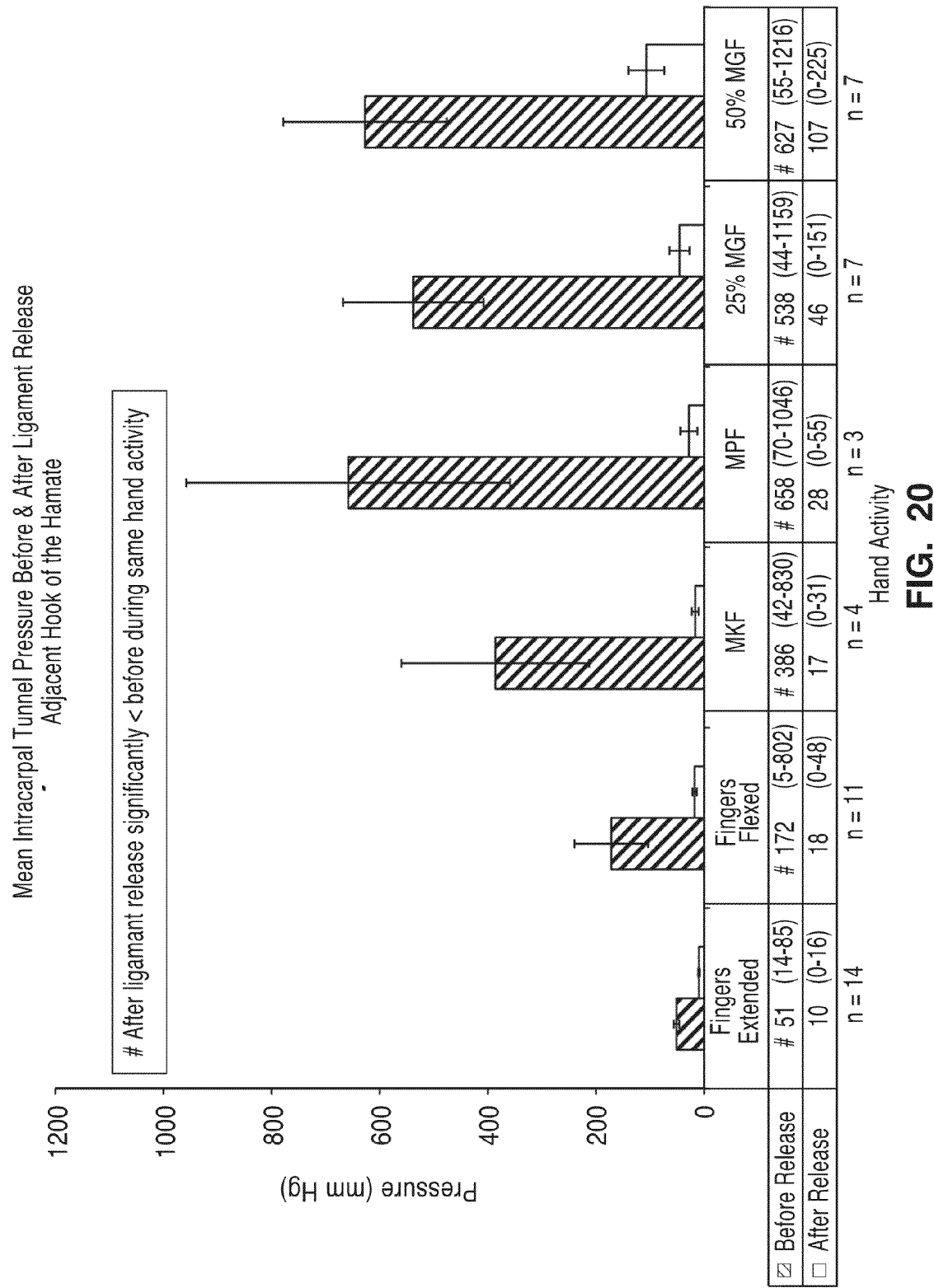
FIG. 20 is a graph comparing mean intracarpal tunnel pressures adjacent HH before and after release of the transverse carpal ligament.

Because of variations in pressure measurement protocol, data from all patients for each hand activity were not included. FIGS. 18-20 indicate the number of patients included for each hand activity.

FIG. 18 compares mean intracarpal tunnel pressures measured at the five standardized proximal-to-distal locations 150 for hand relaxed and pinch activities. Mean pinch forces for MKF and MPF were 49 N (range: 31-64 N) and 45 N (range: 21-78 N), respectively. Measurement location had no significant effect on intracarpal tunnel pressure for the relaxed hands. No significant differences existed between the pressures at any one location when compared with each of the other four locations ($p>0.05$). Measurement location did have a significant effect on intracarpal tunnel pressure during pinch activities. Pressures were significantly greater at HH than at DWC, ⅔ DWC-HH Proximal, and ¾ DWC-HH Distal during both MKF and MPF ($p<0.05$). In addition, pressures were significantly greater at ⅓ DWC-HH Proximal than at DWC during both MKF and MPF ($p<0.05$).

Although there were no significant differences in pressures between MKF and MPF at any of the five locations 150 ($p>0.05$), pinch activities had a significant effect on intracarpal tunnel pressure, but were dependent on location. Compared to hand relaxed, pressures during both MKF and MPF were significantly greater at both ⅓ DWC-HH Proximal and HH ($p<0.05$). In addition, pressures during MPF were significantly greater than those with a relaxed hand at ¾ DWC-HH Distal ($p=0.007$).

During the pressure measurement sequence for each hand activity, a measurement of the pressure at HH was repeated after all other pressures were recorded. This repeat measurement validated the repeatability of the pressure measurement system for each hand activity and patient. For the relaxed hand, MKF, and MPF, the final repeat measurement at HH confirmed that there was no significant difference between the initial and final pressures measured at HH ($p=1$).

FIG. 19 compares mean intracarpal tunnel pressures during hand relaxed, fingers flexed, and grip activities at the five standardized proximal-to-distal locations. Mean grip forces for 25% MGF, 50% MGF, and MGF were 53 N (range: 31-75 N), 98 N (range: 62-139 N), and 185 N (range: 125-281 N), respectively. Measurement location had a significant effect on intracarpal tunnel pressure, but was dependent on hand activity. During MGF, pressures at HH were significantly greater than those at the four other locations ($p<0.05$). In addition, pressures at DWC were significantly less then those at both ⅓ DWC-HH and ¾ DWC-HH Distal (p<0.05). During both 50% MGF and fingers flexed, pressures at HH were significantly greater then those at DWC, ⅔ DWC-HH Proximal, and ¾ DWC-HH Distal (p<0.05). During 25% MGF, only the pressures at DWC were significantly less then those at HH (p=0.03). Also, during fingers flexed, pressures at ⅓ DWC-HH were significantly greater than those at ¾ DWC-HH Distal (p=0.01).

Hand activity had a significant effect on intracarpal tunnel pressure, but was dependent on location. Compared to hand relaxed, pressures during 25% MGF, 50% MGF, and MGF were significantly greater at HH (p<0.05). Pressures during both 50% MGF and MGF were significantly greater than hand relaxed at ⅓ DWC-HH Proximal (p<0.05). At ¾ DWC-HH Distal, only the pressures during MGF were significantly greater than hand relaxed (p<0.0001). At all five locations, the pressures during 50% MGF were not significantly different than during 25% MGF (p>0.05). However, as the grip force increased to MGF, pressures were significantly greater than those during both 25% and 50% MGF at HH (p<0.05). In addition, MGF resulted in significantly greater pressures than 25% MGF at both ⅓ DWC-HH Proximal and ¾ DWC-HH Distal (p<0.05). Again, there were no significant differences between the initial and final pressures measured at HH during any of the hand activities (p=1).

Intracarpal tunnel pressure measured during application of an external force applied to the patient's palm using the grip dynamometer (n=7) was less than the pressure measured during the same force level with the patient actively gripping the same grip dynamometer. Mean intracarpal tunnel pressure (±1 SE) during application of an external force of 25% MGF, 50% MGF, and MGF were 47% (±11%), 49% (±10%), and 49% (±8%), respectively, of the mean pressures measured with the same force levels while the patient was actively gripping.

FIG. 20 compares mean intracarpal tunnel pressures adjacent HH before and after release of the transverse carpal ligament. For all six hand activities, the pressures after ligament division were significantly less than those before (p<0.05).

In summary, intracarpal tunnel pressures were measured in patients with CTS to better understand the magnitude and variability during quantifiable hand activities. Finger flexion, pinch, and grip activities all caused increases in pressure when compared to the relaxed hand. Pressures during each hand activity, as well as relaxed, varied significantly depending on location within the carpal tunnel, with the maximum pressure always occurring adjacent the hook of the hamate. Pressures measured adjacent the hook of the hamate after division of the transverse carpal ligament were significantly lower than those measured before ligament release for the same hand activities.

In this study, the mean peak intracarpal tunnel pressure measured in the relaxed hand of patients with CTS, 56 mm Hg (range: 10-104 mm Hg), was comparable with those previously reported. However, intracarpal tunnel pressures measured during active hand use were substantially greater than those previously reported. The mean peak pressure recorded during MGF was 1151 mm Hg (range: 149-2500 mm Hg). Peak pressures reported by others reached only 319 mm Hg during active power grip. In previous studies, active power grip consisted of a clenched fist without grasping an object. Consequently, active hand use was neither controlled nor quantified. In this study, intracarpal tunnel pressures were recorded in an active hand where the magnitude of the force generated during hand activity was both controlled and quantified.

Several possibilities exist for why intracarpal tunnel pressures of the magnitude observed in this study have not been reported previously. Since pressure is dependent on how forcefully the hand is used and no previous studies measuring pressure during hand use reported the force generated during hand use, one possibility is that patients in this study used their hands more forcefully than those previously. For example, FIG. 19 shows that the mean pressure at HH decreased by 38% and 57% when the grip force was reduced by 50% and 75%, respectively. To ensure that the hand activities were performed accurately by patients in this study, each patient practiced both grip and pinch activities preoperatively, received minimal or no sedation during performance of the hand activities at the time of surgery, and received specific instructions along with visual feedback of their force levels during performance of the hand activities.

A second possibility is that because pressure varies with proximal-distal location within the carpal tunnel, previous studies did not measure the pressure at the location where the peak occurred during active grip. As an example, FIG. 19 shows that if the pressure during MGF were measured 0.6 cm proximal to the center of the hook of the hamate, a 45% reduction in the mean peak pressure occurs. Only one previous study measured pressures from proximal-to-distal within the carpal tunnel in combination with active hand use. However, the proximal-distal locations of the pressure measurements relative to the hook of the hamate, where we recorded the peak pressure, are unknown. In addition, because the magnitude of the grip force was not reported, it is unknown whether its variation may have affected the location where peak pressure was recorded.

Both the type of transducer used for pressure measurement and its calibration range are a third possibility that may have affected previous pressure recordings. In this study, a miniature pressure transducer enclosed in a catheter was placed directly within the carpal tunnel. This type transducer is capable of measuring both hydrostatic and contact pressures combined. All but one of the previous studies reporting pressures during active hand use relied on fluid-filled catheters that measure hydrostatic pressure only. The single study using a catheter-tip based pressure transducer, however, did not quantify the grip force used during pressure measurement.

Initially, the measurement range of the transducer used in this study was inadequate to measure the peak pressures that occurred. The measurement range was increased four times before reaching a final upper limit of 3000 mm Hg that was capable of recording the peak pressures. Only one previous study reported the range of their pressure measurement system. In that study, the maximum pressure measured equaled the limit of the measurement system range, 250 mm Hg. Therefore, it is unknown whether greater pressures occurred.

A fourth possibility is that placement of the pressure transducer relative to both the contents of the carpal tunnel and the flexor retinaculum may affect the pressure measured. In this study, the transducer was inserted from proximal to distal in the carpal tunnel between the contents of the carpal tunnel (tendons, nerve, synovium) and the deep surface of the transverse carpal ligament (TCL). During active finger flexion, the contents of the carpal tunnel shift, causing compression of the median nerve against the TCL by the tensed flexor tendons. Contact between the contents of the carpal tunnel and the deep surface of the TCL also is evident from the volar migration of the contents that exists following carpal tunnel release.

By placing the transducer in this location, it was believed that the maximum contact pressures could be measured between the compliant contents and the more rigid TCL.

While previous research has shown that intracarpal tunnel pressure varies from proximal to distal in patients with CTS, there is a lack of agreement on both how this pressure is distributed and where the maximum pressure occurs. With the wrist in neutral, two different pressure distribution trends were reported. In the first, pressure increased from proximal to distal reaching a maximum at either 1 cm or 3 cm distal to the distal wrist crease and then decreased distally in both relaxed and gripping hands. In the second, pressure variations occurred from proximal to distal reaching a maximum at 4 cm distal to the distal wrist crease in the relaxed hand.

In this study, the pressure distribution trend was similar to the first, increasing from proximal to distal, reaching a maximum, and decreasing distally in both relaxed and active hands. In this study, maximum pressure consistently occurred adjacent the hook of the hamate at a mean distance of 2.0 cm (range: 1.6-2.3 cm) distal to DWC. Because pressure measurements in this study, as well as the others, were obtained at discrete locations, it is not possible to identify the location of the absolute maximum pressure. However, it is evident that a pressure profile that varies as a function of proximal-to-distal position exists whether the hand is passive or active.

In this study, peak intracarpal tunnel pressure coincided with a location adjacent the hook of the hamate. In previous studies that reported pressures at various proximal-to-distal locations in the carpal tunnel, the relationship between the peak pressure and its location relative to the hook of the hamate was not reported. Pressures were measured at fixed distances relative to either the distal wrist crease or the skin incision where the pressure transducer was inserted. Consequently, no information was provided regarding the location of the pressure measurement relative to the hook of the hamate.

Unlike previous studies that measured pressures at fixed distances relative to an external landmark, we chose to standardize the measurement locations based on each patient's hand size. The proximal-to-distal distance from the center of the hook of the hamate to the proximal pisiform was chosen as the reference measurement from which standardized locations for pressure measurement were obtained. Pressure measurements at these standardized locations were referenced to an initial pressure measurement located adjacent the center of the hook of the hamate.

While no previous studies correlated the location of peak intracarpal tunnel pressure with proximity to the hook of the hamate, maximum pressure adjacent the hook of the hamate seems reasonable based on the anatomic configuration of the carpal tunnel. The TCL is defined by its bony attachments to the pisiform, hook of the hamate, tuberosity of the scaphoid, and ridge of the trapezium, making it the stiffest segment of the flexor retinaculum. In this study, pressure was measured using a transducer that measured both hydrostatic and contact pressure combined. The transducer was located between the carpal tunnel contents and the deep side of the TCL. Because the TCL provides significant restraint against movement of the contents of the carpal tunnel, contact pressure would be greater where the ligament is stiffest. Peak pressure beneath the ligament, between its bony attachments, also correlates with the central point of the constricted part of the median nerve in patients with CTS.

Most research reporting intracarpal tunnel pressures neglected the significance of position within the carpal tunnel where pressure was measured. The dynamic behavior of intracarpal tunnel pressure results in significantly different pressures with minor changes in proximal-to-distal position. As shown in FIGS. 18 and 19, these differences become more significant as the hand activity becomes more forceful. Because intracarpal tunnel pressure is a function of proximal-to-distal position within the carpal tunnel, any pressures reported should identify the location where the measurement is taken.

Complete division of the TCL resulted in significantly lower pressures adjacent the hook of the hamate, for all hand activities (FIG. 20). Although the mean intracarpal tunnel pressures for the active hand before ligament division were substantially greater than those reported previously, the mean pressures after ligament division for both the relaxed and active hands were comparable with those previously reported. This significant reduction in intracarpal tunnel pressure validates that considerable contact pressures exist against the deep surface of the TCL prior to its release.

Much of the research on intracarpal tunnel pressure includes investigation of the effect of wrist position on pressure. One limitation of this study was that wrist position was not measured. Although each patient was both instructed to maintain a neutral wrist position during active hand use and practiced each activity preoperatively while maintaining a neutral wrist position, no measurement of wrist position was recorded. While slight variations in wrist position between patients may have affected individual pressures, the intracarpal tunnel pressures reported reflect the natural wrist position for each patient during each hand activity.

Another limitation of this study was the number of patients included in each hand activity. Because of variations in the pressure measurement protocol, not all patients were included in each hand activity at each proximal-to-distal location. While a larger patient population may affect the significance level between the different proximal-to-distal measurement locations and the different hand activities, the general observations reported in this study should remain valid.

While an increase in resting intracarpal tunnel pressure beyond a threshold of 30 mm Hg has been accepted as a primary contributor in patients with CTS, the role of dynamic pressures associated with active hand use remains less apparent. Although increases in intracarpal tunnel pressure during active hand use have been suggested as a possible contributor to CTS, there may be other advantageous functions of these dynamic pressures. The pressures observed in this study provide additional information enabling a new theory regarding the role of dynamic intracarpal tunnel pressures in the etiology of CTS.

Alterations in the mechanical properties of the TCL in patients with CTS have been suggested as a potential factor in the etiology of CTS. In addition, the presence of myofibroblasts in the TCL of patients with CTS suggests that the ligament may be undergoing constant contraction. Others have suggested that the TCL requires regular tensile force to maintain its length and reduce the signs and symptoms of CTS. These observations suggest that morphologic alterations of the TCL may result from an absence of sufficient tensile stress causing it to contract. Consequently, a force imbalance may exist and play a role in the etiology of CTS.

If the TCL requires regular tensile stress to maintain its elastic properties and resist contraction, then dynamic pressures, such as those observed in this study, that occur during forceful hand use may be necessary on a regular basis to provide the tensile stress that the TCL needs. Without this regular stress, the TCL may shorten and become less compliant. A less compliant ligament may reduce the allowable volume that the contents of the carpal tunnel need, thereby increasing the resting pressure. To maintain a balance of forces between the contents of the carpal tunnel attempting to preserve tunnel volume and the TCL trying to contract, a mechanism for the application of this required stress in the TCL must exist. One possibility for increasing stress in the TCL by periodically increasing intracarpal tunnel pressure involves the lumbrical muscles.

The lumbrical muscles migrate proximally into the carpal tunnel during finger flexion and increase pressure in the carpal tunnel. However, finger flexion alone may not be sufficient to produce the tensile stress required for the TCL to maintain its desired morphology. Forceful hand use combined with finger flexion that delivers the lumbrical muscles beneath the TCL with active contraction may be required to adequately stress the TCL, enabling it to maintain its elastic properties. In this study, only when hands were used forcefully were the intracarpal tunnel pressures at their peak. When patient's hands were in a relaxed position with fingers extended and a force applied to the palm of their hand by the physician with the grip dynamometer, intracarpal tunnel pressures were approximately one-half what they were when the patient actively gripped the dynamometer using the same force. Although the data presented in this study has been used to propose this new theory, further investigation is required to better understand the role of force imbalance in the etiology of CTS.

As can be seen, therefore, the present invention includes the following inventive embodiments among others:

1. A method for treating a patient with carpal tunnel syndrome, comprising: identifying a location of the patient's flexor retinaculum suitable for treatment; and injecting an agent into said location of the flexor retinaculum in one or more doses sufficient to weaken the structural integrity of the flexor retinaculum.

2. A method as recited in embodiment 1, wherein the agent comprises one or more doses of collagenase.

3. A method as recited in embodiment 2, wherein the agent comprises a corticosteroid.

4. A method as recited in embodiment 1, wherein identifying a suitable treatment location of the patient's flexor retinaculum comprises: positioning an imaging detector adjacent a region of the patient's hand; the region being associated with the flexor retinaculum, and generating an image of the patient's hand.

5. A method as recited in embodiment 1, wherein the flexor retinaculum includes the transverse carpal ligament.

6. A method as recited in embodiment 1, wherein the flexor retinaculum includes its attachment to the bones.

7. A method as recited in embodiment 4, wherein generating an image comprises positioning an ultrasound transducer adjacent the patient's hand and generating an ultrasound image.

8. A method as recited in embodiment 1, further comprising: increasing the tensile stress in the flexor retinaculum subsequent to injecting said agent.

9. A method as recited in embodiment 8, wherein the increase in tensile stress is generated by pressure within the carpal tunnel, said pressure generated by one or more of the following: having the patient use one or more digits of the hand, having the patient grip the hand around an object; flexing one or more fingers into the palm of the hand and having the patient pinch a thumb and one or more fingers of the hand together.

10. A method as recited in embodiment 9, wherein the object comprises a dynamometer.

11. A method as recited in embodiment 9, wherein the object is pressed into the palm or heel of the patient's hand.

12. A method as recited in embodiment 1, further comprising: measuring pressure within the carpal tunnel 13. A method as recited in embodiment 1, further comprising cutting the flexor retinaculum with a blade.

14. A method as recited in embodiment 4: wherein identifying a suitable treatment location of the patient's flexor retinaculum further comprises computing the palmer-to-dorsal depth from the palm of the hand to the flexor retinaculum; and wherein the agent is injected via a needle at said computed palmer-to-dorsal depth along an axis substantially parallel to an imaging surface of the detector.

15. A method as recited in embodiment 1: wherein identifying a suitable treatment location of the patient's flexor retinaculum further comprises computing the palmer-to-dorsal depth from the palm of the hand to the flexor retinaculum; and wherein the agent is injected via a needle at said computed palmer-to-dorsal depth along an axis substantially parallel to a longitudinal axis of the flexor retinaculum.

16. A method as recited in embodiment 1, wherein the agent is delivered at a central portion of the flexor retinaculum.

17. A method as recited in embodiment 1, further comprising: inserting a guide tube into the hand adjacent the flexor retinaculum; and accessing the flexor retinaculum at the distal end of the guide tube.

18. A method as recited in embodiment 17, further comprising: advancing a pressure sensor within said guide tube to said treatment location; and measuring the pressure at said location.

19. A method as recited in embodiment 17, further comprising: advancing a cutting probe within said guide tube to said treatment location; and cutting tissue associated with the flexor retinaculum.

20. A system for treating a patient with carpal tunnel syndrome, comprising: a needle guide; an injection needle; the needle guide comprising a guide hole configured for receiving the injection needle; and an agent configured for delivery within said injection needle to a tissue region associated with the flexor retinaculum of the patient; wherein said agent is configured to weaken the structural integrity of the flexor retinaculum.

21. A system as recited in embodiment 20, further comprising: a clamp coupled to the needle guide; wherein the clamp comprises a reference surface for positioning at a palm of the patient's hand; wherein the needle guide is slideably coupled to the clamp such that the needle guide may be adjusted with respect to the reference surface.

22. A system as recited in embodiment 21, wherein the longitudinal axis of the guide hole is substantially parallel to the reference surface.

23. A system as recited in embodiment 21, further comprising an imaging device configured for imaging the carpal tunnel during injection; wherein the clamp is configured to house the imaging device.

24. A system as recited in embodiment 23, wherein the imaging device is pivotably coupled to the clamp to allow for transverse and longitudinal images of the carpal tunnel to be obtained.

25. A system as recited in embodiment 23, wherein the imaging device comprises an imaging surface; wherein the imaging surface is substantially parallel to the longitudinal axis of the guide hole of the needle guide.

26. A system as recited in embodiment 25, wherein the needle guide is configured to be adjusted in a palmar-dorsal direction while the longitudinal axis of the guide hole remains substantially parallel to the imaging surface.

27. A system as recited in embodiment 21, wherein the clamp and needle guide comprise an indicator configured to indicate a depth of needle insertion with respect to the reference surface.

28. A system as recited in embodiment 20, further comprising: a guide tube disposed within the guide hole; the guide tube configured to be inserted into the hand adjacent the flexor retinaculum; wherein the guide tube comprises a central channel sized to accommodate delivery of an instrument to the tissue region.

29. A system as recited in embodiment 28, further comprising: a pressure sensor sized to be received within said guide tube to be delivered to the tissue region; wherein the pressure sensor is configured to measuring the pressure at said location.

30. A system as recited in embodiment 28, further comprising: a cutting probe sized to be received within said guide tube to be delivered to the tissue region; and the cutting probe configured to cut tissue associated with the flexor retinaculum.

31. A system as recited in embodiment 21, further comprising: a linkage attached to the clamp; wherein the linkage is configured to couple to the patients hand; wherein the linkage comprises a first joint that allows rotation of the clamp with respect to the hand.

32. A system as recited in embodiment 31, wherein the first joint is configured to allow rotation of the clamp in a flexion-extension direction with respect to the patient's hand.

33. A system as recited in embodiment 32, the linkage further comprising: a second joint; wherein the second joint is configured to allow rotation of the clamp in a radial-ulnar direction with respect to the patient's hand.

34. A system as recited in embodiment 31, wherein the linkage is configured to allow proximal to distal translation of the of the clamp with respect to the patient's hand.

35. A system as recited in embodiment 33, the linkage further comprising: a third joint; wherein the third joint is configured to allow rotation of the clamp in a internal-external direction with respect to the patient's hand.

36. An apparatus for treating a patient with carpal tunnel syndrome, comprising: a needle guide; an injection needle; the needle guide comprising a guide hole configured for receiving the injection needle; and a clamp coupled to the needle guide; wherein the clamp comprises a reference surface for positioning at a palm of the patient's hand; wherein the needle guide is slideably coupled to the clamp such that the needle guide may be adjusted with respect to the reference surface.

37. An apparatus as recited in embodiment 36, further comprising: an imaging device configured for imaging the carpal tunnel during injection; wherein the clamp is configured to house the imaging device 38. An apparatus as recited in embodiment 36, further comprising: an agent configured for delivery within said injection needle to a tissue region associated with the flexor retinaculum of the patient; wherein said agent is configured to weaken the structural integrity of the flexor retinaculum.

39. An apparatus as recited in embodiment 36, wherein the longitudinal axis of the guide hole is substantially parallel to the reference surface.

40. An apparatus as recited in embodiment 36, wherein the imaging device is pivotably coupled to the clamp to allow for transverse and longitudinal images of the carpal tunnel to be obtained.

41. An apparatus as recited in embodiment 37, wherein the imaging device comprises an ultrasound transducer having an imaging surface; wherein the imaging surface is substantially parallel to the guide hole of the needle guide.

42. An apparatus as recited in embodiment 36, wherein the needle guide is configured to be adjusted in a palmar-dorsal direction while the longitudinal axis of the guide hole remains substantially parallel to the reference surface.

43. An apparatus as recited in embodiment 36, wherein the clamp and needle guide comprise an indicator configured to indicate a depth of needle insertion with respect to the reference surface.

44. An apparatus as recited in embodiment 36, further comprising: a guide tube disposed within the guide hole; the guide tube configured to be inserted into the hand adjacent the flexor retinaculum; wherein the guide tube comprises a central channel sized to accommodate delivery of an instrument to the tissue region.

45. An apparatus as recited in embodiment 44, further comprising: a pressure sensor sized to be received within said guide tube to be delivered to the tissue region; wherein the pressure sensor is configured to measuring the pressure at said location.

46. An apparatus as recited in embodiment 44, further comprising: a cutting probe sized to be received within said guide tube to be delivered to the tissue region; wherein the cutting probe is configured to cut tissue associated with the flexor retinaculum.

47. An apparatus as recited in embodiment 36, further comprising: a linkage attached to the clamp; wherein the linkage is configured to couple to the patients hand; wherein the linkage comprises first and second joints that allow rotation of the clamp with respect to the hand; wherein the first joint is configured to allow rotation of the clamp in a flexion-extension direction with respect to the patient's hand; and wherein the second joint is configured to allow rotation of the clamp in a radial-ulnar direction with respect to the patient's hand.

48. An apparatus for treating a patient with carpal tunnel syndrome, comprising: a base configured to support a patient's forearm and hand; the base comprising a first surface configured to support the forearm and a second surface configured to support the hand; wherein the second surface is adjacent to the first surface and disposed at an angle with the first surface; and a pivotable arm coupled to the base; wherein the pivotable arm is configured to support a needle guide.

49. An apparatus as recited in embodiment 49, the needle guide comprising a guide hole configured for receiving an injection needle.

50. An apparatus as recited in embodiment 48, further comprising: a clamp coupling the pivotable arm and the needle guide; wherein the needle guide is slideably coupled to the clamp such that the needle guide may be adjusted with respect to the second surface.

51. An apparatus as recited in embodiment 49, further comprising: an agent configured for delivery within said injection needle to a tissue region associated with the flexor retinaculum of the patient; wherein said agent is configured to weaken the structural integrity of the flexor retinaculum.

52. An apparatus as recited in embodiment 50, further comprising: an imaging device configured for imaging the carpal tunnel during injection; wherein the clamp is configured to house the imaging device.

53. An apparatus as recited in embodiment 49, wherein the pivotable arm is configured to allow positioning of the longitudinal axis of the guide hole to be substantially parallel to the longitudinal axis of the flexor retinaculum when the hand is supported on said second surface.

54. An apparatus as recited in embodiment 48, wherein the needle guide is configured to be adjusted in a palmar-dorsal direction while the longitudinal axis of the guide hole remains substantially parallel to the second surface.

55. An apparatus as recited in embodiment 50, wherein the clamp and needle guide comprise an indicator configured to indicate a depth of needle insertion with respect to the reference surface.

56. An apparatus as recited in embodiment 48, wherein the pivotable arm allows translation and rotation of the needle guide with respect to the second surface.

57. An apparatus as recited in embodiment 56, wherein the pivotable arm comprises a first joint that allows rotation of the clamp in a flexion-extension direction with respect to the second surface.

58. An apparatus as recited in embodiment 57, the pivotable arm further comprising: a second joint; wherein the second joint is configured to allow rotation of the clamp in a radial-ulnar direction with respect to the second surface.

59. An apparatus as recited in embodiment 57, wherein the pivotable arm is configured to allow proximal to distal translation of the of the clamp with respect to the second surface.

60. An apparatus as recited in embodiment 58, the pivotable arm further comprising: a third joint; wherein the third joint is configured to allow rotation of the clamp in a internal-external direction with respect to the second surface.

61. A method for treating a patient with carpal tunnel syndrome, comprising: identifying a location of the patient's flexor retinaculum suitable for treatment; and cutting at least a portion of the flexor retinaculum.

62. A method for treating a patient with carpal tunnel syndrome, comprising: identifying a location of the patient's carpal tunnel suitable for treatment; and delivering an agent into the carpal tunnel synovium of the patient.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for treating a patient with carpal tunnel syndrome, comprising:
    providing a needle guide comprising a guide hole configured for receiving an injection needle;
    wherein a clamp is coupled to the needle guide;
    the clamp being configured to house an imaging device;
    positioning a reference surface of the clamp at a palm of the patient's hand;
    slideably adjusting the needle guide with respect to the reference surface of the clamp;
    wherein an imaging surface of the imaging device is substantially parallel to a longitudinal axis of the guide hole of the needle guide;
    imaging the flexor retinaculum with respect to surrounding tissue during injection with the imaging device;
    inserting said injection needle to a tissue region associated with the flexor retinaculum of the patient; and
    injecting an agent into said location of the flexor retinaculum in one or more doses sufficient to weaken the structural integrity of the flexor retinaculum.

2. A method as recited in claim 1, wherein the agent further comprises one or more doses of collagenase or a corticosteroid.

3. A method as recited in claim 1, wherein the flexor retinaculum includes the transverse carpal ligament.

4. A method as recited in claim 1, wherein the flexor retinaculum includes its attachment to the bones.

5. A method as recited in claim 1, wherein imaging the flexor retinaculum comprises generating an ultrasound image.

6. A method as recited in claim 1, further comprising: increasing the tensile stress in the flexor retinaculum subsequent to injecting said agent.

7. A method as recited in claim 6, wherein the increase in tensile stress is generated by pressure within the carpal tunnel, said pressure generated by one or more of the following: having the patient use one or more digits of the hand, having the patient grip the hand around an object; flexing one or more fingers into the palm of the hand and having the patient pinch a thumb and one or more fingers of the hand together.

8. A method as recited in claim 7, wherein the object comprises a dynamometer.

9. A method as recited in claim 7, wherein the object is pressed into the palm or heel of the patient's hand.

10. A method as recited in claim 1, further comprising: measuring pressure within the carpal tunnel.

11. A method as recited in claim 1, further comprising: cutting the flexor retinaculum with a blade.

12. A method as recited in claim 1, further comprising:
    identifying a suitable treatment location of the patient's flexor retinaculum by computing the palmer-to-dorsal depth from the palm of the hand to the flexor retinaculum; and
    wherein the agent is injected via a needle at said computed palmer-to-dorsal depth along an axis substantially parallel to a longitudinal axis of the flexor retinaculum.

13. A method as recited in claim 1, wherein the agent is delivered at a central portion of the flexor retinaculum.

14. A method as recited in claim 1, further comprising:
    orienting the imaging device with respect to the clamp to obtain transverse and longitudinal images of the flexor retinaculum.

15. A method as recited in claim 1, further comprising:
    adjusting the needle guide in a palmar-dorsal direction while the longitudinal axis of the guide hole remains substantially parallel to the imaging surface.

16. A method for treating a patient with carpal tunnel syndrome, comprising:
    providing a needle guide comprising a guide hole configured for receiving an injection needle;
    wherein a clamp is coupled to the needle guide;
    the clamp being configured to house an imaging device;

slideably adjusting the needle guide with respect to a reference surface of the clamp;

wherein a linkage is attached to the clamp;

wherein the linkage comprises a first joint that allows rotation of the clamp with respect to the hand;

wherein the clamp is configured to rotate about the first joint in a palmar-dorsal direction with respect to the patient's hand to couple a reference surface of the clamp to a palm of the patient's hand;

inserting said injection needle to a tissue region associated with the flexor retinaculum of the patient; and injecting an agent into said location of the flexor retinaculum in one or more doses sufficient to weaken the structural integrity of the flexor retinaculum.

17. A method as recited in claim 16, the linkage further comprising a second joint oriented perpendicular to the first joint, the method further comprising:

rotating the clamp about the second joint in a radial-ulnar direction with respect to the patient's hand.

18. A method as recited in claim 17, the linkage further comprising a third joint oriented perpendicular to the first joint and second joint, the method further comprising:

rotating the clamp about the third joint in an internal-external direction with respect to the patient's hand.

19. A method as recited in claim 16, further comprising:

translating the clamp proximal to distal at the linkage with respect to the patient's hand.

\* \* \* \* \*